US012788792B2

(12) United States Patent
Al-Dosary

(10) Patent No.: US 12,788,792 B2
(45) **Date of Patent: *Nov. 10, 2026**

(54) **METHOD FOR TREATING A SKIN WOUND CONTAINING *KLEBSIELLA PNEUMONIAE***

(71) Applicant: Imam Abdulrahman Bin Faisal University, Dammam (SA)

(72) Inventor: Sahar K. Al-Dosary, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 165 days.

This patent is subject to a terminal disclaimer.

(21) Appl. No.: 18/828,511

(22) Filed: Sep. 9, 2024

(65) Prior Publication Data

US 2024/0424046 A1 Dec. 26, 2024

Related U.S. Application Data

(63) Continuation of application No. 18/490,805, filed on Oct. 20, 2023, now Pat. No. 12,121,559, which is a continuation of application No. 18/336,614, filed on Jun. 16, 2023, now Pat. No. 11,826,393, which is a continuation of application No. 17/707,132, filed on Mar. 29, 2022, now Pat. No. 11,738,060, which is a continuation of application No. 15/943,494, filed on Apr. 2, 2018, now Pat. No. 11,324,791.

(51) Int. Cl.
*A61K 39/108* (2006.01)
*A61K 36/324* (2006.01)
*A61K 39/09* (2006.01)
*A61P 31/04* (2006.01)

(52) U.S. Cl.
CPC ........ *A61K 36/324* (2013.01); *A61K 39/0266* (2013.01); *A61K 39/092* (2013.01); *A61P 31/04* (2018.01); *A61K 2236/333* (2013.01)

(58) Field of Classification Search
None
See application file for complete search history.

(56) References Cited

U.S. PATENT DOCUMENTS

| | | | |
|---|---|---|---|
| 9,138,451 B2 | 9/2015 | Popp | |
| 11,324,791 B2 | 5/2022 | Al-Dosary | |
| 11,738,060 B2 | 8/2023 | Al-Dosary | |
| 11,826,393 B2 * | 11/2023 | Al-Dosary | A61P 31/04 |
| 12,121,559 B2 * | 10/2024 | Al-Dosary | A61K 36/324 |
| 2019/0083561 A1 | 3/2019 | Kreuter | |

FOREIGN PATENT DOCUMENTS

| | | |
|---|---|---|
| KR | 611248 B1 | 8/2006 |
| WO | WO 2004/076680 A2 | 9/2004 |
| WO | WO 2010/036938 A2 | 1/2010 |
| WO | WO 2014061715 | 5/2014 |

OTHER PUBLICATIONS

Hasson SS, et al. "In vitro antibacterial activity of three medicinal plants—*Boswellia* (*Luban*) species," Asian Pacific Journal of Tropical Biomedicine (2011)S178-S182 (5 pages).
Dahiya, et al. "Phytochemical Screening and Antimicrobial Activity of Some Medicinal Plants Against Multi-drug Resistant Bacteria from Clinical Isolates," Indian Journal of Pharmaceutical Sciences (2012), Sep.-Oct. vol. 74, Issue 5, pp. 443-450 (14 pages).
Kozlowska, et al. "Chemical Composition and Antibacterial Activity of Some Medicinal Plants From *Lamiaceae* Family," Acta Poloniae Pharmaceutica—Drug Research, (2015), vol. 72 No. 4 pp. 757-767 (11 pages).
Anzlovar, et al., "Essential Oil of Common Thyme as a Natural Antimicrobial Food Additive," Food Technol. Biotechnol. (2014) 52 (2), pp. 263-268 (6 pages).
Al-Juraifani, Amal A., "Antimicrobial Activity of Some Medicinal Plants Used in Saudi Arabia," Canadian Journal of Pure and Applied Sciences, (2011), vol. 5, Issue Jun. 2, 2011 (6 pages).
Ali et al. Chinese Medicine 6: 1-14, 2011.
Bishnu Joshi, et al., "Phytochemical extraction and antimicrobial properties of different medicinal plants: *Ocimum sanctum* (Tulsi), *Eugenia caryophyllata* (Clove), *Achyranthes bidentata* (Datiwan) and *Azadirachta indica* (Neem)", Journal of Microbiology and Antimicrobials, vol. 3, No. 1. Jan. 2011. pp. 1-7.
Hidayat Hussain, et al., "Retracted: Chemistry and Biology of Essential Oils of Genus *Boswellia*", Evidence-Based Complementary and Alternative Medicine, Article ID: 605304, 2014, 1 page.
Hidayat Hussain, et al., "Erratum to Chemistry and Biology of Essential Oils of Genus *Boswellia*", Evidence-Based Complementary and Alternative Medicine, Article ID: 792517, 2014, 2 pages.
Ali A. Shareef, "Evaluation of antibacterial activity of essential oils of *Cinnamomum* sp. and *Boswe//ia* sp.", Journal of Basrah Researches {(Sciences)). vol. 37, No. 5.A, 2011, pp. 60-71.
Shaik Mannur Ismail, et al., "Antimicrobial activity of frankincense of Boswe//ia serrata", International Journal of Current Microbiology and Applied Sciences, vol. 3, No. 10, 2014, pp. 1095-1101.
Amir Farshchi, et al., "Effects of *Boswellia papyrifera* Gum Extract on Learning and Memory in Mice and Rats", Iranian Journal of Basic Medical Sciences, vol. 13, No. 2, 2010, pp. 9-15.
S. de Rapper, et al., "The additive and synergistic antimicrobial effects of select frankincense and myrrh oils—a combination from the pharaonic pharmacopoeia", Letters in Applied Microbiology, vol. 54, 2012, pp. 352-358.
Arieh Moussaieff, et al.. "Boswellia resin: from religious ceremonies to medical uses; a review of in-vitro, in-vivo and clinical trials", Journal of Pharmacy and Pharmacology, vol. 61, 2009, pp. 1281-1293.
Seyed Mohammad Nabavi, et al., "Plants belonging to the genus *Thymus* as antibacterial agents: From farm to pharmacy", Food Chemistry, vol. 173. 2015, pp. 339-347.
Zeinab Lakis, et al., "The Antimicrobial Activity of Thymus Vulgaris and Origanum Syriacum Essential Oils on *Staphylococcus aureus*, *Streptococcus pneumoniae* and Candida Albicans", Farmacia. vol. 60, No. 6. 2012, pp. 857-865.

(Continued)

*Primary Examiner* — S. Devi
(74) *Attorney, Agent, or Firm* — Oblon, McClelland, Maier & Neustadt, L.L.P.

(57) ABSTRACT

A method for treating a microbial infection, especially pneumonia, comprising
administering an aqueous-ethanol extract of *Thymus* or *Boswellia* or a composition containing
the extract. Aqueous-ethanol extracts of *Thymus* and/or *Boswellia*.

4 Claims, 3 Drawing Sheets

(56) References Cited

OTHER PUBLICATIONS

Aamir Javed, et al.,•Jn vitro Evaluation of the Synergistic Antimicrobial Effect of Boswellia Sacra and Nigella Sativa, Essential Oil on Human Pathogenic Microbial Strains, American Journal of Phytomedicine and Clinical Therapeutics, vol. 3, No. 2, 2015, pp. 185-192.
Maria Fournomiti, et al., "Antimicrobial activity of essential oils of cultivated oregano (*Origanum vulgare*), sage (*Salvia officinalis*). and thyme (*Thymus vulgaris*) against clinical isolates of *Escherichia coli*. Klebsiella oxyloca, and Klebsiella pneumoniae", Microbial Ecology in Health and Disease, vol. 26, 2015, pp. 1-7.
Monika Sienkiewicz, et al., "The Antimicrobial Activity of Thyme Essential Oil Against Multidrug Resistant Clinical Bacterial Strains", Microbial Drug Resistance, vol. 18, No. 2, 2012, pp. 137-148.
Hasnia Benmoussa, et al., "Effect of extraction methods on kinetic, chemical composition and antibacterial activities of *Tunisian thymus vulgaris*. L. essential oil". Separation Science and Technology, vol. 51, No. 13. 2016. pp. 2145-2152.
Hercules Sakkas et al., "In vitro antimicrobial activity of five essential oils on multidrug resistant Gram-negative clinical isolates", Journal of Intercultural Ethnopharmacology, vol. 5. Issue 3, 2016, pp. 212-218.
Ahmed Al-Harrasi, et al., "Phytochemical Analysis of the Essential Oil from Botanically Certified Oleogum Resin of *Boswellia sacra* (Omani Luban)", Molecules, vol. 13, 2008, pp. 2181-2189.
M. Z. Siddiqui, et al., Boswellia Serrata, A Potential Antiinflammatory Agent: An Overvieo'l', Indian Journal of Pharmaceutical Sciences, May-Jun. 2011, pp. 255-261.
Kathleen Gerbeth, et al., "Determination of major boswellic acids in plasma by high-pressure liquid chromatography/mass spectrometry", Journal of Pharmaceutical and Biomedical Analysis, vol. 56, Issue 5, Dec. 15, 2011, pp. 998-1005 (Abstract only).
King-Thom Chung et al., Effects of benzidine and benzidine analogues on growth of bacteria including Azotobacter vinelandit, Environmental Toxicology and Chemistry. vol. 17, Issue 2, Oct. 26, 2009, 3 pages (Abstract only).
Pascale Goupy, et al., "Antioxidant composition and activity of barley (*Hordeum vulgare*) and malt extracts and of isolated phenolic compounds", Journal of the Science of Food and Agriculture, vol. 79. 1999. pp. 1625-1634.
Pirjo Mattila, et al., "Determination of Flavonoids in Plant Material by HPLC with Diode-Array and Electro-Array Detections", J. Agric. Food Chem., vol. 48. No. 12, 2000, pp. 5834-5841.
Firas A. Al-Bay a Ti, "Synergistic antibacterial activity between Thymus vulgaris and Pimpinella anisum essential oils and methanol extracts". Journal of Ethnopharmacology, vol. 116. 2008, pp. 403-406.
Ayyad VV. Al-Shahwany, et al., •Antibacterial and Anti-biofilm Activity of Three Phenolic Plant Extracts and Silver Nanoparticles on *Staphylococcus aureus* and Klebsiella pneumoniae, Biomedicine and Biotechnology, vol. 4, No. 1, 2016, pp. 12-18.
Jorge M. Alves-Silva, et al., "Chemical composition and in vitro antimicrobial, antifungal and antioxidant properties of essential oils obtained from some herbs widely used in Portugal", Food Control, vol. 32, 2013, pp. 371-378.
Hasan Baydar, et al., "Antibacterial activity and composition of essential oils from *Origanum*, *Thymbra* and *Satureja* species with commercial importance in Turkey", Food Control, vol. 15, 2004, pp. 169-172.
Alina A. Dobre, et al.. "Antibacterial Profile of Essential Oils Against Pathogen Bacteria", Bulletin UASVM Agriculture, vol. 69, No. 2, 2012, pp. 255-261.
S.A. Burt. et al., "Antibacterial activity of selected plant essential oils against *Escherichia coli* O157:H?", Letters in Applied Microbiology, vol. 36. 2003. pp. 162-167.
I. M. Kh. Al-Aubadi, et al., "Chemical composition of thyme seeds *Thymus vulgaris* and its antimicrobial activity", ISSN: 1992-7479. vol. 2, No. 9, 2011, pp. 295-305 (with English Abstract).
Maria C. Rota, et al., "Antimicrobial activity and chemical composition of Thymus vulgaris Thymus zygis and Thymus hyemalis essential oils", Food Control, vol. 19, 2008, pp. 681-687.
Filomena Nazzaro, et al., "Effect of Essential Oils on Pathogenic Bacteria", Pharmaceuticals, vol. 6, 2013, pp. 1451-1474.

* cited by examiner

METHOD FOR TREATING A SKIN WOUND CONTAINING *KLEBSIELLA PNEUMONIAE*

CROSS-REFERENCE TO RELATED APPLICATIONS

The present application is a Continuation of U.S. application Ser. No. 18/490,805, now U.S. Pat. No. 12,121,559, having a filing date of Oct. 20, 2023, which is a Continuation of U.S. application Ser. No. 18/336,614, now U.S. Pat. No. 11,826,393, having a filing date of Jun. 16, 2023 which is a Continuation of U.S. application Ser. No. 17/707,132, now U.S. Pat. No. 11,738,060, having a filing date of Mar. 29, 2022 which is a Continuation of U.S. application Ser. No. 15/943,494, now U.S. Pat. No. 11,324,791, having a filing date of Apr. 2, 2018.

BACKGROUND ON THE INVENTION

Field of the Invention

The invention involves the fields of microbiology, pharmacology, herbology and medicine. It is directed to particular extracts and compositions thereof of *Thymus* (Thyme) and *Boswellia* that exhibit antimicrobial properties against microorganisms, especially against *Streptococcus pneumoniae.*

Description of the Related Art

This "background" description provides a general context helpful in understanding the invention. The work of the presently named inventor(s) to the extent that it is described in this section, as well as aspects of the description which may not otherwise qualify as prior art at the time of filing, are neither expressly or impliedly admitted as prior art against the present invention.

According to the World Health Organization (WHO), pneumonia is a common, but serious illness, especially in developing countries. About 15% of children, who die under the age of five, die from pneumonia. A major cause of pneumonia in infants, as well as in patients in hospital intensive care units is *Klebsiella pneumoniae.*

Existing antibiotic treatments for *Klebsiella pneumoniae* and other types of pneumonia caused by bacteria are threatened by emergent antibiotic resistance.

Medicinal plants have traditionally been used to treat diseases and promote health all over the world and have high economic value (Joshi et al., "Phytochemical extraction and antimicrobial properties of different medicinal plants: *Ocimum sanctum* (Tulsi), *Eugenia caryophyllata* (Clove), *Achyranthes bidentata* (Datiwan) and *Azadirachta indica* (Neem)", JOURNAL OF MICROBIOLOGY AND ANTIMICROBIALS, Vol. 3, No. 1. January 2011. pages 1-7).

*Boswellia* is a genus of medicinal plants (see FIG. 1) that was used in 11th century by Persian physician and philosopher Avicenna for the treatment of inflammation of the urinary tract. About 75% of the *Boswellia* species are found in northeast Africa, however, this genus, which includes both trees and shrubs, contains at least twenty species widespread in the dry regions spanning from West Africa to Arabia, south to the northeast region of Tanzania, and also in Madagascar and India.

Gums and resins obtained from *Boswellia* (see FIG. 2) contain essential oils and oligomers which have medicinal properties including immune enhancing, antibacterial, anti-inflammatory, wound healing and anticancer properties (Shareef, "Evaluation of antibacterial activity of essential oils of *Cinnamomum* sp. and *Boswellia* sp.", JOURNAL OF BASRAH RESEARCHES (SCIENCES). Vol. 37, No. 5. A, 2011, pages 60-71). *Boswellia* gums and resins are traditionally used as diuretics and for treatment of diarrhea, dysentery, cardiac disease, cough, hemorrhage, dyspnea, polyuria, urinary troubles, piles, ulcers and burns (Ismail et al., "Antimicrobial activity of frankincense of *Boswellia serrata*", INTERNATIONAL JOURNAL OF CURRENT MICROBIOLOGY AND APPLIED SCIENCES, Vol. 3, No. 10, 2014, pages 1095-1101). Current research has focused on studying the effects of *Boswellia* extracts on memory regions of the brain (Farshchi et al., "Effects of *Boswellia papyrifera* Gum Extract on Learning and Memory in Mice and Rats", IRANIAN JOURNAL OF BASIC MEDICAL SCIENCES, Vol. 13, No. 2, 2010, pages 9-15).

*Boswellia* gums and resins are also the source of frankincense, which is mentioned several times in the Bible, and which is used as incense in many religious and cultural ceremonies (De Rapper et al., "The additive and synergistic antimicrobial effects of select frankincense and myrrh oils—a combination from the pharaonic pharmacopoeia", LETTERS IN APPLIED MICROBIOLOGY, Vol. 54, 2012, pages 352-358. Frankincense is an oligomer resin that is extracted by tapping the inner bark of *Boswellia* trees.

*Thymus* is also a genus of medicinal plants, commonly known as Thyme. Members of this genus are native to Europe and are found around the Mediterranean basin and northern Europe, as well as other parts of the world such as Asia, South America, and Australia (Nabavi et al., "Plants belonging to the genus *Thymus* as antibacterial agents: From farm to pharmacy", FOOD CHEMISTRY, Vol. 173. 2015, pages 339-347).

Thyme is used in traditional medicine for the treatment of coughs, upper respiratory infections, acute and chronic bronchitis, whooping cough, and for respiratory system disorders due to its antitussive, antioxidant, anti-inflammatory, and antimicrobial properties. Thyme is also employed for external use as a mouth wash in gargles to treat laryngitis.

Recent research suggests that the essential oil of thyme, which contains carvacrol and thymol, has advantageous anti-inflammatory properties. Thymol and carvacrol are phenolic compounds which have strong antifungal properties as well as other therapeutic properties (Lakis et al., "The Antimicrobial Activity of *Thymus vulgaris* and *Origanum syriacum* Essential Oils on *Staphylococcus aureus, Streptococcus pneumoniae* and *Candida albicans*", FARMACIA. Vol. 60, No. 6. 2012, pages 857-865). Thymol may reduce resistance of some bacteria to some antibiotics such as penicillin.

Previous studies indicated the antimicrobial activity of *Boswellia* and thyme extracts, especially against *Klebsiella pneumoniae* (Javed et al., "In vitro Evaluation of the Synergistic Antimicrobial Effect of *Boswellia sacra* and *Nigella sativa*, Essential Oil on Human Pathogenic Microbial Strains", AMERICAN JOURNAL OF PHYTOMEDICINE AND CLINICAL THERAPEUTICS, Vol. 3, No. 2, 2015, pages 185-192). However, the essential oils of *Boswellia sacra* and *Nigella saliva* showed fewer antibacterial effects.

Frankincense obtained from *Boswellia serrata* was shown to inhibit *Klebsiella pneumoniae*. In this study, the antibacterial activity of frankincense was tested against various bacteria isolates. These included isolates from Gram positive bacteria, including *Bacillus subtilis, Staphylococcus aureus*, and *Streptococcus pneumoniae*, and from Gram negative bacteria, including (*E. coli, Klebsiella pneumoniae, Enterobacter aerogenes, Pseudomonas aeruginosa*, and *Proteus vulgaris*. Its antibacterial effects were compared with those of the antibiotic ciprofloxacin as positive control and against DMSO as a negative control. The results showed that *Klebsiella pneumoniae* was sensitive against high concentrations of frankincense extracts of *Boswellia serrata*. However, studies comparing the antibacterial effects of cinnamon essential oil and frankincense essential oil bacterial isolates of *E. coli, Staphylococcus aureus, Pseudomonas aeruginosa, Brucella* sp., *Klebsiella pneumoniae* and *Proteus* sp. showed that the minimum inhibitory concentration ("MIC") of frankincense essential oil was less than those of cinnamon oil. In fact, *Klebsiella pneumoniae* was less sensitive to cinnamon oil and gave negative results with frankincense oil; however, frankincense essential oil showed good antimicrobial activity against the other tested bacteria.

Fournomiti et al. ("Antimicrobial activity of essential oils of cultivated oregano (*Origanum vulgare*), sage (*Salvia* AY *officinalis*) and thyme (*Thymus vulgaris*) against clinical isolates of *Escherichia coli, Klebsiella oxyloca*, and *Klebsiella pneumoniae*", MICROBIAL ECOLOGY IN HEALTH AND DISEASE, Vol. 26, 2015, pages 1-7) investigated the antimicrobial activity of some medicinal plant extracts: oregano (*Origanum vulgare*), sage (*Salvia officinalis*), and thyme (*Thymus vulgaris*) against three clinical bacteria isolates (*E. coli, Klebsiella oxytoca, Klebsiella pneumoniae*); results showed that *Klebsiella pneumoniae* was the second most sensitive strain and thyme followed by oregano essential oils were the most efficient.

Sienkiewicz et al. ("The Antimicrobial Activity of Thyme Essential Oil Against Multidrug Resistant Clinical Bacterial Strains", MICROBIAL DRUG RESISTANCE, Vol. 18, No. 2, 2012, pages 137-148) screened the antimicrobial activity of thyme essential oil against clinical multidrug resistant strains of *Staphylococcus, Enterococcus, Escherichia*, and *Pseudomonas*; results indicated that thyme essential oil strongly inhibited the growth of the tested clinical strains.

Recently Benmoussa et al. ("Effect of extraction methods on kinetic, chemical composition and antibacterial activities of Tunisian *Thymus vulgaris*. L. essential oil". SEPARATION SCIENCE AND TECHNOLOGY, Vol. 51, No. 13. 2016, Pages 2145-2152) used four methods for extraction of the volatile compounds from Tunisian *Thymus vulgaris* leaves: microwave-assisted hydrodistillation (MAHD), solvent-free microwave extraction (SFME), hydrodistillation (HD) and steam distillation (SD). Results showed that *T. valgaris* essential oils had antibacterial effect against multi-drug resistant bacteria, and SFME method was efficient and gave high antimicrobial activity which was attributed to 17 volatile compounds and high monoterpense hydrocarbons content. Thus it was postulated that SFME is the best alternative method for essential oils extraction.

Sakkas et al. ("In vitro antimicrobial activity of five essential oils on multidrug resistant Gram-negative clinical isolates", JOURNAL OF INTERCULTURAL ETHNOPHARMACOLOGY, Vol. 5. Issue 3, 2016, pages 212-218) studied the efficacy of five essential oils (Basil, chamomile blue, origanum, thyme, and tea tree oil) on three gram negative and positive clinical isolates (*Acinetobacter baumannii, E. coli, K. pneumoniae* and *P. aeruginosa*) using a broth macrodilution method, however, antibacterial activity against these multi-drug resistant isolates was poor.

Prior studies report conflicting results with regard to inhibition of microorganisms and are difficult to compare because *Thymus* and *Boswellia* extracts were prepared from different materials, solvents, and procedures. Alternative extraction procedures produce materially different extracts because different components are extracted or are extracted at different rates by the different solvents, for example carbohydrates tend to be extracted more readily in aqueous solutions like water (polarity index 9), while more hydrophobic components like boswellic acids in less hydrophilic solvents like methanol (polarity index 5.1) or ethanol (polarity index 5.2). Polar substances tend to dissolve better in polar solvents, while non-polar substances dissolve better in nonpolar solvents. Thus, a mixture of ethanol and water will have different extractive properties than either water alone or 95% ethanol alone.

The inventors sought to investigate the effects of extraction of *Thymus* and *Boswellia* with an aqueous-ethanol solution containing substantially equivalent amounts of water and ethanol in order to determine whether such an extraction solvent would produce extracts with a better, different, or broader spectrum of antimicrobial activity and to evaluate antimicrobial activity of these extracts on microorganisms causing pneumonia.

SUMMARY OF THE INVENTION

Aqueous-ethanol extracts of *Thymus* and *Boswellia* were tested on strains of bacteria that cause pneumonia: *Streptococcus pneumoniae* and *Klebsiella pneumoniae*. As shown herein, an aqueous-ethanol extract of *Boswellia* exhibited a higher antibacterial activity as determined by both zone of inhibition tests and by determination of minimal inhibitory concentrations exhibited a high degree of anti-bacterial activity on a spectrum of clinical isolates of *Streptococcus pneumoniae*. Surprisingly, the addition of the aqueous-ethanol *Thymus* extract to the aqueous-ethanol *Boswellia* extract did not produce synergistic or additive antibacterial activity and in some cases appeared to antagonize anti-bacteria activity compared to antimicrobial activity of the *Boswellia* extract by itself.

Another aspect of the invention is to provide methods for treating infections caused by Gram-positive bacteria or Gram-negative bacteria, especially by respiratory pathogens such as *Streptococcus pneumoniae* or *Klebsiella pneumoniae* using components of an aqueous-ethanol *Boswellia* or *Thymus* extract.

A further aspect of the invention is to provide methods for preventing the growth or colonization of a subject or object with Gram-positive or Gram-negative bacteria, especially in or around the respiratory tract using compositions containing the aqueous-ethanol extracts of *Boswellia* or *Thymus*, or both.

An additional aspect of the invention is to provide a method for promoting wound healing, including healing of mucous membranes and tissues of the respiratory system, using components of an aqueous-ethanol *Boswellia* or *Thymus* extract.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
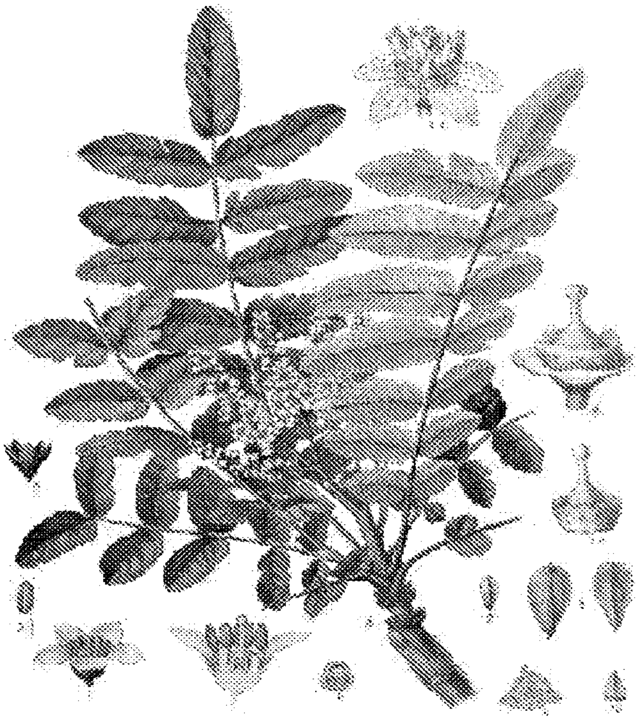
FIG. 1 illustrates the leaves and flowers of a *Boswellia* species.
Figure 2:
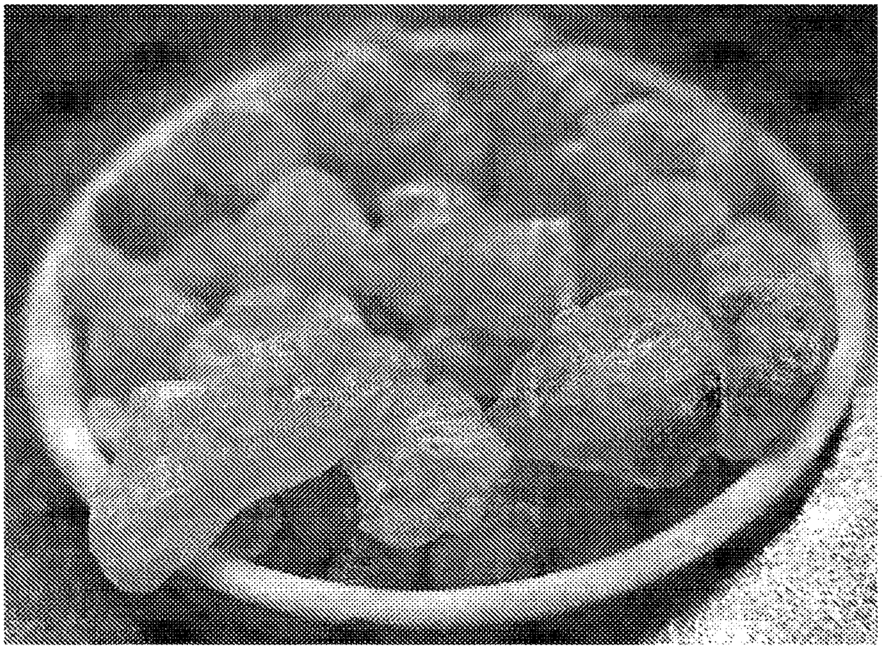
FIG. 2 is a photo of frankincense extracted from *Boswellia*.
Figure 3:
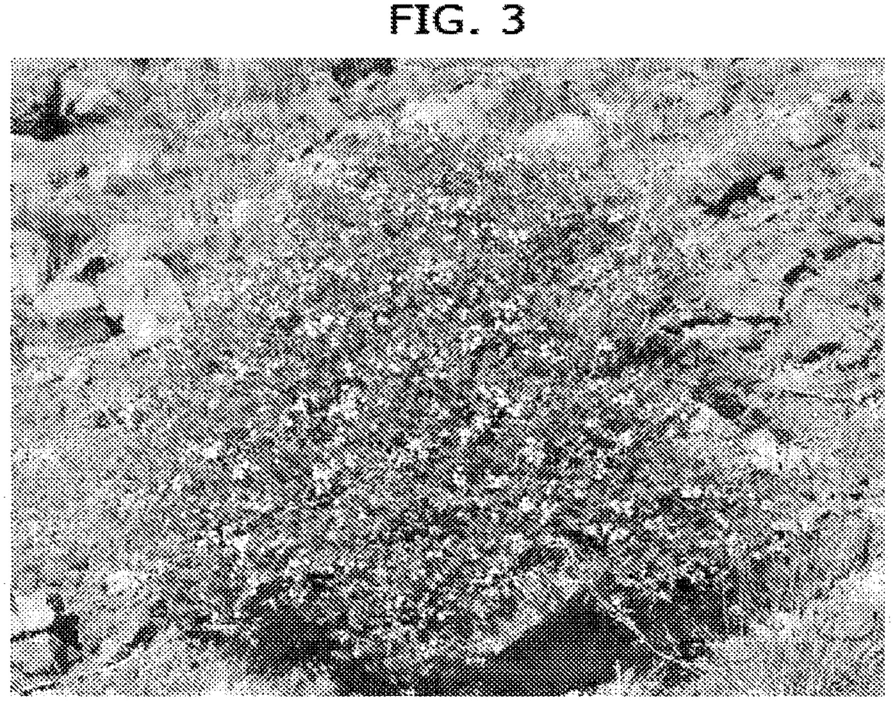
FIG. 3 is a photo of a *Thymus* species.

Embodiments of the present disclosure will now be described more fully hereinafter with reference to the accompanying drawings, in which some, but not all embodiments of the disclosure are shown.

*Boswellia* is a genus of trees and shrubs that includes the following species: *Boswellia sacra* (*B. bhaw-dajiana*), *B. carterii, B. frereana, B. serrata* (*B. thurifera*). *Boswellia* contains flavonoids and phenolic compounds. A *Boswellia* extract may be obtained from one or more of these species.

*Boswellia* gum or oleo-gum resin is prepared by milking a *Boswellia* tree for its sap usually by cutting a slot in the tree and letting the sap run out. Traditional preparation of *Boswellia* gum includes a month-long waiting period where the water leaves this gum as it hardens; which results in a final product of 30-60 wt % resin, 5-10 wt % essential and aromatic oils which are mostly monoterpenes such as E-beta-ocimene and limonene; Al-Harrasi A, Al-Saidi S. *Phytochemical analysis of the essential oil from botanically certified oleogum resin of Boswellia sacra* (Omani Luban). *Molecules*. Vol. 13, 2008, pages 2181-2189 (incorporated by reference), with the final 30-55% consisting of polysaccharides; Siddiqui M Z. *Boswellia serrata, A potential antiinflammatory agent: an overview. Indian J Pharm Sci.* pp. 255-261, 2011 (incorporated by reference). *Boswellia* gum also contains boswellic acids, including α-boswellic acid and β-boswellic acid, acetylated forms of these acids, and 11-keto-β-boswellic acid (KBA) and 512.74 for 3-O-acetyl-11-keto-β-boswellic acid (AKBA); Gerbeth K, et al. *Determination of major boswellic acids in plasma by high-pressure liquid chromatography/mass spectrometry. J. Pharm. Blamed. Anal.* Vol. 56, Issue 5, Dec. 15, 2011, pages 998-1005 (incorporated by reference).

Oil of frankincense is produced by steam distillation of the *Boswellia* tree resin. The oil's chemical components include monoterpenes, sesquiterpenes, monoterpenoles, sesquiterpenols and ketones.

*Thymus*. Thyme is an aromatic perennial evergreen herb with culinary, medicinal, and ornamental uses. The most common variety is *Thymus* vulgaris also known as *Thymus aestivus, T. ilerdensis* or *T. velantianus*. Thyme is of the genus *Thymus* of the mint family, and a relative of the oregano genus *Origanum*. *Thymus* contains flavonoids and phenolic compounds.

Thyme oil may be extracted from the fresh or partly dried flowering tops and leaves of the plant by water or steam distillation. The main chemical components are a-thujone, a-pinene, camphene, b-pinene, p-cymene, a-terpinene, linalool, borneol, b-caryophyllene, thymol and carvacrol.

Aqueous-Ethanol Extraction. An aqueous-ethanol extract is prepared by mashing, macerating, blending, sonicating, freeze-thawing, French pressing, digesting, or otherwise disrupting *Boswellia* gum-resin or *Thymus* leaves so that soluble components can be removed and recovered. Generally extraction is performed in an aqueous-ethanol solution which may contain salt(s), buffers, stabilizers, enzymes, chelators (e.g., of divalent cations or metals like iron), antioxidants and/or preservatives. A solution for aqueous-ethanol extraction will contain sufficient water and ethanol to extract the components of *Boswellia* gum resin or *Thymus* that are soluble in aqueous-ethanol.

In some embodiments of the invention, *Boswellia* gum (or seeds, flowers, leaves, bark, roots, or other plant components) and/or *Thymus* leaves (or seeds, flowers, stems, roots or other *Thymus* components) are extracted with an aqueous-ethanol solvent. An extract may made from fresh *Boswellia* or *Thymus* materials, or, alternatively, from dried, frozen or otherwise preserved materials, such as dried gum-resin or dried leaves and flowers.

Such an extract is advantageously produced by extracting *Boswellia* gum-resin or *Thymus* leaves with an aqueous-ethanol solution containing between about 20-80 wt % water and about 80-20 wt % ethanol, preferably, between about 40-60 wt % water and about 60-40 wt % ethanol, and most preferably about 50 wt % water and about 50 wt % ethanol. These ranges include all intermediate values and subranges.

The extraction may be made using a single aqueous-ethanol phase or may be made using a multiple phase extraction, such as with an aqueous-ethanol solvent in combination with one or more immiscible phases; e.g., in combination with a substantially immiscible hydrophobic solvent.

In some embodiments soluble components of *Boswellia* gum resin or *Thymus* leaves are extracted by a gaseous or vaporous aqueous-ethanol solvent.

In other embodiments extraction may be performed under acidic, neutral or alkaline conditions ranging from pH 1.0 to pH 14.0 and all intermediate subranges and values. These include extraction at a pH of 2.0, 2.5, 3.0, 3.5, 4.0, 4.5, 5.0, 5.5, 6.0, 6.5, 7.0, 7.5, 8.0, 8.5 or 9.0. In one embodiment, extraction is performed at a pH ranging from 6.0 to 8.0. In other embodiments, solvent extract is performed without adjustment of the pH of the aqueous-ethanol solvent.

In some embodiments, extraction times range from ≤5, 10, 15, 30, or 60 minutes, or 1, 2, 3, 4, 5, 6, 7, 8, 9, 10, 11, 12, 15, 18, 20, 24 or more hours. The extraction may be continued until at least 5, 10, 25, 50, 60, 75, 80, 90, 95, 9, or 100% of the soluble components in the source material are dissolved in the extraction solvent. This range includes all intermediate values.

To facilitate the extraction of soluble components, surfactants, chelators, and/or enzymes that digest *Thymus* leaves or components of *Boswellia* gum-resin, such as cellulase (e.g., endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulase (CMCase), avicelase, celludextrinase, cellulase A, cellulosin AP, alkali cellulase, cellulase A 3, 9.5 cellulase, and pancellase SS), proteases (e.g., serine-, cysteine-, threonine-, aspartic-, glutamic-, or metallo-proteases, and asparagine peptide lyases), or nucleases (RNAase, DNAase), may be used.

Extraction may be performed at different temperatures, for example, from 0, 5, 10, 15, 20, 25, 30, 35, 40, 45, 50, 55, 60, 65, 70, 75, 80, 85, 90, 95, or 100° C. (or at higher temperatures under pressure) or any intermediate temperature within this range.

A *Boswellia* gum-resin or *Thymus* extract can be further purified by removing insoluble or solid components from an aqueous-ethanol extract, for example, by separating these solid components from liquid components by centrifugation or filtration. Protein and non-protein components may be separated or isolated from one another by filtration, precipitation, chromatography or by addition of a protease.

Proteins may be isolated by the chromatographic procedures described herein or by precipitation, and/or differential solubilization.

Oils and hydrophobic components removed by aqueous-ethanol extraction may be separated from aqueous components by phase partition based on their differential solubility in non-polar solvents, such as a solvent having a dielectric constant of less than 15, 10, 5, or 2. Nonpolar solvents include chloroform, diethylether, hexanes, benzene and toluene.

An extract can be dialyzed to remove salts or other cations and anions or other low molecular weight solutes. Dialysis membranes having molecular weight cutoffs ranging from 1, 5, 10, 50, 100, 500, 1,000, 5,000, 10,000, 50,000, 100,000, 500,000 or 1,000,000 kDa or any endpoint or intermediate cutoff value within this range may be employed for this purpose. Dialysis may also be used for solvent exchange, for example, to selectively remove alcohol and/or water.

A dialysis buffer can be selected to effect solvent exchange in an extract, for example, to alter the ionic concentration or pH of an extract.

One skilled in the art can select an appropriate dialysis buffer, temperature, and duration, for example, dialysis may be performed at 4° C. or at 25° C. for 2, 4, 6, 8, 10, 12, 18, or 24 hours. Dialysis buffer may be replaced and dialysis repeated 1, 2 or more times if desired.

An aqueous-ethanol extract may be further purified chromatographically. For example, it may be fractionated by size exclusion chromatography, affinity chromatography, HPLC, hydrophobic interaction chromatography, ion-exchange chromatography or free-flow electrophoresis by methods known to those skilled in the art.

A *Boswellia* gum-resin or *Thymus* extract may be further treated to render it stable, aseptic or sterile. Such methods include but are not limited to filtration, heat pasteurization or sterilization, addition of chelators such as EDTA, EGTA, vitamin C or other antioxidants, or oxidants such as hydrogen peroxide. Microbial contaminants may be removed by filtration, for example, through a 0.1, 0.2, 0.22, or 0.45 micron filter. A fresh extract may be refrigerated, frozen, or lyophilized for storage or stored in the absence of oxygen, for example, under a nitrogen or inert gas atmosphere.

A purified *Boswellia* gum resin or *Thymus* aqueous-ethanol extract, preferably one having the solid components removed, can be concentrated by removing all or a portion of the aqueous-ethanol solvent. A concentrated extract will have a lower concentration of water and/or ethanol and higher relative concentration of water-ethanol soluble components from *Boswellia* gum resin or *Thymus* than an original or starting extract. A concentrated extract may contain 1, 5, 10, 20, 30, 40, ≤50 wt % of water or the aqueous solvent contained in the original extract. This range includes any intermediate value.

An anhydrous, dry or desiccated *Boswellia* gum-resin or *Thymus* extract will have substantially all of the aqueous-ethanol solvent removed from it, for example, an anhydrous, dry or dessicated extract may contain no more than 0.1, 0.5, 1, 5, or 10 wt % water, ethanol, or water and ethanol.

Concentration and dehydration methods are known in the art and include, but are not limited to, those performed with a device such as hot air blower, dryer, cylindrical dryer, zeolite dryer, a desiccator, or a freeze-dryer. An extract can be concentrated or dried by evaporating the solvent using a falling film device, low pressure evaporator, or spray tower.

A fresh, concentrated, or dried extract may be stored under sterile or aseptic conditions that prevent loss of its antimicrobial activity, for example, the extract may be stored in liquid nitrogen, or at −86° C., −70° C., −20° C., 4° C., stored in desiccated form in sealed ampules, or stored under nitrogen or an inert atmosphere.

Standarization of *Boswellia* or *Thymus* extracts. The aqueous-ethanol extract of the invention may be standardized by removal of the water and ethanol solvent from components extracted from *Boswellia* gum or resin, weighing the residuum (non-water, non-ethanol components that dissolved in or were retained in the aqueous-ethanol solvent used for extraction), and admixing, dissolving or suspending the residuum to a desired concentration in a composition. For example, a known weight of the residuum may be admixed with known weight of a solid excipient; a known weight of residuum may be dissolved in a solvent, such as in fresh aqueous-ethanol solution; or a known weight of the residuum may be resuspended in a polar or non-polar solvent, optionally in the presence of a surfactant, stabilizer, buffer or other excipient. The final concentration of the residuum may range from at least 0.001, 0.005, 0.01, 0.05, 0.1, 0.5, 1, 2, 3, 4, 5, 6, 7, 8, 9, 10, 20, 30, 40, 50, 60, 70, 80, 90, <100 wt % based on the combined weight of the residuum and other components in a final composition. In some embodiments, any solid components in a raw aqueous-ethanol extract will be removed by centrifugation or filtration, e.g., through a 0.45 micron or 0.22 micron filter which can also serve to remove microorganisms to produce a purified or sterile solution.

The activity of an extract may also be standardized based on a quantifiable degree of antimicrobial, biocidal, bioinhibitory, wound or tissue healing activity, or other biological activity. For bacteria, including gram-positive, gram-negative, and mycobacteria, these include standardization based on minimal inhibitory concentration or on size of a zone of inhibition produced by a known amount or concentration of an extract on a test or control bacterial strain, such as on a *Streptococcus pneumoniae* or *Klebsiella pneumoniae* strain obtained from a depository such as the ATCC. Activity on non-bacterial microorganisms, such as viruses, yeasts, fungi, parasites, or neoplasms may also be determined using conventional assays as can other functional activities of an extract such as on promotion of wound or tissue healing.

The term "composition" includes those with one or more ingredients. Thus, an original aqueous-ethanol extract of *Boswellia* or *Thymus* without further additions is a composition. A composition may contain fewer components than those present in an original aqueous-ethanol extract. For example, it can omit water, ethanol, or salts present in an original aqueous-ethanol extract or it may consist of the anhydrous and ethanol-free components of a gum-resin or leaf extract.

In some embodiments a composition will contain one or more ingredients, one or more combinations of ingredients, or a greater content of an ingredient, than those or that present in an original aqueous-ethanol extract. For example, it may contain one or more preservatives, antioxidants, chelators, or pharmaceutically acceptable carriers or excipients not present in an original *Boswellia* or *Thymus* aqueous-ethanol extract or it may be a combination of a *Boswellia* or *Thymus* extract and an extract of another plant. In some embodiments, a composition will contain both a *Boswellia* and a *Thymus* extract.

A composition may contain at least 0.001, 0.05, 0.1, 0.2, 0.5, 1.0, 2.0, 3.0, 4.0, 5.0, 6.0, 7.0, 8.0, 9.0, 10, 15, 20, 25, 30, 35, 40, 45, 50, 55, 60, 65, 70, 75, 80, 85, 90, 95, 99 or 100 wt % (or any endpoint or intermediate value within this range) of a *Boswellia* or *Thymus* extract, for example, it may contain 0.1-10 wt % of an anhydrous and ethanol-free *Boswellia* and/or *Thymus* extract and 99.9-90 wt % water or other carrier or excipient. Preferably, a composition will contain a therapeutically effective amount of an extract.

A composition containing an extract of the invention may be formulated for therapeutic use, for example, with a pharmaceutically acceptable excipient or excipient in aseptic or sterile form. It may also include other therapeutically active ingredients, such as anesthetics, plant extracts, antibiotics, or other antimicrobial agents.

In some embodiments, the composition of the invention will incorporate one or more non-*Boswellia* or *Thymus* antimicrobial or antiviral herbal extracts. Such herbs include *Calendula officinalis, Cinnamomum zeylanicum, Syzygium aromaticum, Allium sativum, Echinacea angustifolia, Mahonia aquifolium, Althaea officinalis* L.), *Usnea barbata, Arctostaphylos uva-ursi, Achillea millefolium, Astragalus membranaceus, Uncaria tomentosa, Vaccinium macrocarpon, Sambucus nigra, Zingiber officinale, Melissa officinalis, Glycyrrhiza glabra, Verbascum Thapsus, Olea europaea*, and/or *Origanum vulgare*. These herbal extracts include the oil and oily or dry components of these herbs as well as their components soluble in water or in an aqueous-ethanol solution.

In other embodiments a *Boswellia* or *Thymus* extract of the invention may be formulated along with, or used or administered in conjunction with, traditional remedies prepared from alum, anise, arak, asafetida, banana, black seed (*Nigella sativa*), caraway, cardamom, chamomile, cucumber, frankincense, garlic, myrrh, nakhwa, petroleum (naft, batrul), pomegranate, saffron, thyme, turmeric, or walnut bark. Treatments and modes of administration are incorporated by reference to hypertext transfer protocol ://_archive.aramcoworld.com/issue/200605/natural.remedies.of.arabia.htm (last accessed Apr. 13, 2017). Plant extracts may be in the form of an aqueous, alcohol or other organic solvent, or oily extract, may be in dry or powdered form, or may contain purified active components from these traditional remedies.

In other embodiments, extracts from cruciferous vegetables or chemical components of cruciferous vegetables may be added or incorporated into a composition containing a *Boswellia* or *Thymus* aqueous-ethanol extract. Cruciferous vegetables contain high levels of carotenoids, tocopherols, and ascorbic acid which can add to the favorable properties of an aqueous-ethanol extract of *Boswellia* or *Thymus.*

Advantageously a composition will contain a concentration of *Boswellia* or *Thymus* extract and/or other active ingredients, sufficient to prevent or inhibit the growth of a target microorganism such as the Gram positive bacteria like *S. pneumoniae* described herein. When a composition includes both the *Boswellia* or *Thymus* extract and another active ingredient it may exhibit additive or synergistic therapeutic and/or antimicrobial activity, or the mixture of two active ingredients may expand its antimicrobial spectrum.

In some embodiments, the therapeutic or antimicrobial *Boswellia* or *Thymus*-based compositions will be formulated for application to wounds in skin or mucous membranes, such as epidermal wounds or wounds in the eyes, nose or the mouth. For example, in the treatment of eye infections or other infections of mucous membranes, the composition, in the form of a solution, wash, lotion, emulsion, ointment or a cream, can be applied to the mucous membrane of the patient using standard techniques. Standard methods known in the medical and pharmaceutical arts are used to formulate and apply these compositions to wounds.

In the treatment of mouth infections, including gingivitis, the composition may be formulated as a solution or cream can be applied using a sponge applicator or a toothbrush. It may also be incorporated into a gargling solution, mouthwash or rinse.

The compositions of the invention may also be in the form of a solution and used for infusing into a body cavity (e.g., a surgical wash) and thereby treating or reducing the risk of infection or may be prepared in an inhalable or aerosol form for administration to the respiratory system.

In other embodiments, the composition is formulated as a wound dressing or bandage can that can provide sustained contact or release of a *Boswellia* or *Thymus* extract with a wound and inhibit the growth of Gram-positive bacteria and other microorganisms while also preventing contamination or desiccation of a wound.

Formulations. A composition containing the *Boswellia* or *Thymus* aqueous-ethanol extract may be provided in various forms. Formulations may include other active ingredients and/or non-toxic, inert pharmaceutically suitable excipients such as solid, semisolid or liquid diluents, fillers, or adjuvants.

Formulations may be in solid, semisolid or viscous, liquid, atomized, aerosol or vaporous forms. They may have an acidic or basic pH and may contain water and/or organic ingredients such as alcohols and other conventional organic excipients, such as those used in pharmaceutical or cosmetic products. A formulation may be in the form of a solution, tincture, wash (e.g., surgical or dental washes), foam, spray, serum, gel, suppository, suspension, emulsion, cream, lotion, paste, ointment, granule, powder, freeze-dried or desiccated form, troche, capsule, tablet, or pill. An antiseptic or cleaning formulation may contain ingredients conventionally included in such products such as water, organic compounds, chelators, surfactants, oxidants and disinfectants. The particular formulations described in detail below may contain chelators or antioxidants as well as other conventional excipients or carriers.

Chelators. Compositions according to the invention may incorporate one or more chelators that can sequester elements like calcium or iron necessary for bacterial growth. Examples of chelators of iron and calcium include, but are not limited to, diethylene triamine pentaacetic acid (DTPA), ethylene diamine tetraacetic acid (EDTA), nitrilotriacetic acid (NTA), 1,3-propylene diamine tetraacetic acid (PDTA), Ethylene diamine disuccinic acid (EDDS), and ethylene glycol tetraacetic acid (EGTA). Any suitable chelating agent known in the art, which is biologically safe and able to chelate iron, calcium or other metals, is suitable for the invention. Suitable biocompatible chelating agents useful in conjunction with the present invention include, without limitation, monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), citric acid, pharmaceutically acceptable salts thereof, and combinations of any of the foregoing. Other exemplary chelating agents include: phosphates, e.g., pyrophosphates, tripolyphosphates, and hexametaphosphates. Such chelators may be incorporated in amounts sufficient to bind to the divalent cations or metals, such as iron, in a composition or in a wound to which the composition is applied. For example, the concentration may be selected to bind to at least 25, 50, 75 or 100 mole % of the calcium, magnesium, or iron in a composition or wound.

Antioxidants. Antioxidants suitable for use in pharmaceutical, cosmetic, and food products are known. BHT (butylated hydroxytoluene) and BHA (butylated hydroxyanisole) are two common oil soluble antioxidants. Tocopherols (Vitamin E derivatives, e.g., alpha-tocopherol) and ascorbyl palmitate may also be used. Ascorbates, such as vitamin C, and propyl gallate are examples of water soluble antioxidants. Alpha lipoic acid, acetyl carnitine, Coenzyme Q10

(ubiquinol), selenium, retinoic acid, B vitamins, flavonoids, and various algae and plant extracts may also be used as antioxidants. Such antioxidants can be incorporated in amounts sufficient to quench free radicals in a composition or in a wound to which the composition is applied. For example, the concentration may be selected to bind to at least 25, 50, 75 or 100 mole % of the free radicals in a composition or wound.

Customary Ingredients and Excipients. In addition to the active ingredient(s), the formulations described herein, depending on their particular physical and chemical formulation may contain the customary excipients, for example animal and vegetable fats, waxes, paraffins, starch, tragant or cellulose derivatives, polyethylene glycols, silicones, bentonites, silicic acid, talcum, and zinc oxide, or mixtures of these substances.

Aqueous suspensions may contain customary excipients such as liquid diluents, for example water, ethyl alcohol, propylene glycol, suspending agents, for example ethoxylated isostearyl alcohols, polyoxyethylene sorbit and sorbitan esters, microcrystalline cellulose, aluminum metahydroxide, bentonite, agar-agar and tragant, or mixtures of these substances.

The kinds of formulations mentioned herein may also contain colorants, preservatives and odor- and flavor-enhancing additives, for example peppermint oil and eucalyptus oil, and, for ingestible products sweeteners and flavorings. Solutions and emulsions according to the invention may contain the customary excipients such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethyl formamide, oils, in particular cottonseed oil, peanut oil, corn oil, olive oil, castor oil and sesame oil, glycerin, glycerol formal, tetrahydrofurfuryl alcohol, polyethylene glycols and fatty acid esters of sorbitan, or mixtures of these substances.

Some specific kinds of formulations of compositions containing an aqueous-ethanol extract of *Boswellia* or *Thymus* are described below.

Topical formulations. Topical formulations include antimicrobial pharmaceuticals, deodorants, soaps, body washes, shampoos, lubricants (e.g., for catheters or other devices, anatomical sites, or surfaces at risk of microbial contamination), hand or skin sanitizers and disinfectants and personal care products (e.g., a product that is used for personal hygiene). A topical formulation can be provided in a variety of formulations including but not limited to solutions, tinctures, gels, serums, creams, colloids, emulsions, lotions, solid sticks, aerosols or dry powders as described in U.S. Pat. Nos. 4,844,902; 6,818,226; 6,469,015; 7,147,854; 7,192,607; 7,205,003; and 7,252,831, each of which is hereby incorporated by reference in its entirety.

Aqueous solutions. The *Boswellia* or *Thymus* extract of the invention may be dissolved in water, another solvent miscible with water, or a mixture thereof. It may contain other solutes or liquid components such as salts, chelators (e.g., EDTA, EGTA), antioxidants, or preservatives. In some embodiments it may further comprise an acid, a base, or buffer for adjusting or stabilizing the pH of a composition so as to maintain or maximize antibacterial activity of the *Boswellia* or *Thymus* extract or for suitability for treatment of a particular type of wound. For example, the acid or base is useful for adjusting the pH of a composition to a pH of about 1 to about 14 (e.g., from about 1 to about 2, from about 2 to about 2, from about 3 to about 4, from about 4 to about 5, from about 5 to about 6, from about 6 to about 7, from about 7 to about 8, from about 8 to about 9, from about 9 to about 10, from about 10 to about 11, from about 11 to about 12, from about 12 to about 13, from about 13 to about 14, or any other value or range of values therein). In certain embodiments, the pH of the composition ranges from about 3.5 to about 13; in other embodiments, from about 6.5 to about 8.5. In some embodiments, the pH is about 13; in other embodiments, the pH is about 7.5 to about 8.4. In certain embodiments, the pH of the present composition ranges from about 5 to about 13; from about 6 to about 13; from about 7 to about 13; from about 8 to about 13; from about 9 to about 13; from about 10 to about 13; from about 11 to about 13; from about 12 to about 13. Such pH adjustment can improve the dispersibility of ingredients present in an aqueous-ethanol composition.

Acids useful in the present compositions include inorganic acids such as carbonic acid, sulfuric acid, or hydrochloric acid. Organic acids can alternatively be employed. Suitable organic acids include $C_1$ to $C_{20}$ organic acids such as formic acid, citric acid, malic acid, adipic acid, tannic acid, lactic acid, ascorbic acid, acetic acid, fumaric acid, and mixtures thereof. In one embodiment, the acid is citric acid. In some embodiments, the compositions do not comprise an acid. These ranges include all intermediate values as well as endpoints.

Bases useful in the present compositions may be organic or inorganic bases. Suitable inorganic bases include alkali metal or alkaline earth metal compounds such as sodium hydroxide, lithium hydroxide, potassium hydroxide, sodium carbonate, potassium carbonate, sodium bicarbonate, potassium bicarbonate, magnesium carbonate and calcium carbonate. Other suitable bases include ammonium hydroxide, substituted amine bases and ammonia. In some embodiments, the compositions do not comprise a base. These ranges include all intermediate values as well as endpoints.

In other embodiments, the compositions can comprise one or more salts. Salts useful in the present compositions include organic or inorganic salts. Suitable salts include alkali or alkaline earth metal salts such as sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate. The salt can present in the compositions in an amount from 0 wt % to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein) of the composition. In some embodiments, the salt is present from about 0.01 wt % to about 0.05 wt % of the compositions. In some embodiments, the compositions do not contain a salt.

In other embodiments the compositions contain water or solvents miscible with water or a mixture of both. A composition may contain an amount of *Boswellia* or *Thymus* extract that exhibits antimicrobial or therapeutic (e.g., wound healing, etc.) activity in combination with an amount of solvent sufficient to keep the extract in solution or to dissolve a dry extract. In some embodiments, the amount of solvent in the present compositions can range from about 10 to about 90 wt % (e.g., about 10 wt % to about 15 wt %, about 15 wt % to about 20 wt %, about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, about 50 wt % to about 55 wt %, about 55 wt % to about 60 wt %, about 60 wt % to about 65 wt %, about 65 wt % to about 70 wt %, about 70 wt % to about 75 wt %, about 75 wt % to about 80 wt % A), about 80 wt % to about 85 wt %, about 85 wt % to about 90 wt %, or any other value or range of values therein). In certain embodiments, the compositions comprise from about 80 wt % to about 90 wt % water or about 90 wt. % to about <100 wt. % water.

The present compositions can further comprise an organic solvent, in the absence or presence of water in an amount sufficient to keep the extract in solution or to dissolve a dry extract. Suitable organic solvents include, but are not limited to, $C_1$ to $C_4$ alcohols such as methanol, ethanol, n-propanol and i-propanol, n-butanol, sec-butanol, isobutanol and tert-butanol. Alternatively, glycols such as ethylene glycol, propylene glycol and polyethylene glycol, and ketone-containing solvents such as acetone can be employed. In certain embodiments, the aqueous organic solvent is ethanol or i-propanol. In one embodiment, the compositions comprise water and an alcohol; in another embodiment, water and ethanol or i-propanol. The amount of organic solvent, if present, can be selected based on factors such as its miscibility in water, if present, and the amount of *Boswellia* or *Thymus* extract. In some embodiments, the organic solvent can be present in the compositions in an amount ranging from 0 wt % to about 10 wt %) (e.g., 0 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, or any other value or range of values therein) of the composition. In some embodiments, the compositions do not comprise an organic solvent.

The compositions of the invention can further contain one or more other additives. Suitable additives include, but are not limited to, detergents, as surface tension modifiers, flocculants, dispersants, rheology modifiers, emulsifiers, surfactants, chelators, and solvents. Illustrative additives are polysorbates, oils (e.g., canola oil, vegetable oils, etc.). In some embodiments, the additive(s) can be present in the compositions in amounts ranging from 0 to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % A) to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein) of the composition.

In some embodiments the present compositions will contain a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants that can be present in the compositions of the invention include anionic surfactants, amphoteric surfactants, cationic surfactants, zwitterionic surfactants, non-ionic surfactants, and combinations thereof. Surfactants suitable for use in the present invention can include polysorbates such as polysorbate 20, polysorbate 40, polysorbate 60 or polysorbate 80. An amount of surfactant that is sufficient to emulsify other ingredients in a composition or that is sufficient to lower surface tension of a pharmaceutical composition so as to maximize contact between a wound and the *Boswellia* or *Thymus* extract or maximize antimicrobial activity may be selected.

Serums. A serum refers to a light, quickly absorbed composition that exposes and permits rapid uptake of an active ingredient by skin. It can be used as an alternative to heavier creams or lotions that contain occlusive, or airtight, moisturizing ingredients such as petrolatum or mineral oil that keep water from evaporating. Serums usually contain fewer lubricating and thickening agents, like nut or seed oils, than creams or lotions. Most serums are water-based or based on hydrophilic components, eliminating oils altogether. A serum may be formulated to contain a higher concentration of an active ingredient, such as *Boswellia* or *Thymus* extract, than a cream or lotion.

Gels. Gels provided herein include semi-solid suspensions that contain a *Boswellia* or *Thymus* extract. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic. In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinyl alcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In another embodiment, the organic macromolecules having a stabilizing action include long-chain linear high molecular weight polysaccharides with a molecular weight of more than one million. In this embodiment, 0.1 to 1.5 wt % of such stabilizers are included. In another embodiment, a uniform gel can be prepared by adding dispersing agents such as alcohol or glycerin. In another embodiment, the organic macromolecules can be dispersed by trituration, mechanical mixing or stirring, or combinations thereof. In another embodiment, the liquid can be either water or all water-miscible solvents. Examples of applicable solvents include alkanols, such as ethanol and isopropyl alcohol, benzyl alcohol, propylene glycol and similar solvents.

Creams/Emulsions. Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. The oil phase can comprise petroleum jelly and a fatty alcohol, such as cetyl or stearyl alcohol. The aqueous phase can contain a humectant. The emulsifier can be a nonionic, anionic, cationic or amphoteric surfactant. In one embodiment, the oil phase includes, but is not limited to, cetyl alcohol, stearyl alcohol, stearic acid, liquid paraffin, and dimethicone. In another embodiment, the water phase ingredient includes, but is not limited to, glycerol and ethyl paraben as well as *Boswellia* or *Thymus* aqueous-ethanol extract. In another embodiment, the emulsifying agent includes, but is not limited to, fatty alcohol polyoxyethylene ether (PEREGAL™ A-20), polyoxylstearate (SG-6), or combinations thereof.

Lotions. Lotions provided herein include liquids or semi-liquid formulations that are generally lower in viscosity than a cream or gel. The lotions can be an oil-in-water formulation stabilized by a surface-active agent and are usually suitable for application to unbroken skin. In one embodiment, the lotions contain suspending agents to produce better dispersions and compounds useful for localizing and holding the active agent such as components of a *Boswellia* or *Thymus* aqueous-ethanol extract in contact with the skin, including methylcellulose, sodium carboxymethyl-cellulose, and similar compounds.

Ointments. Ointments provided herein include semi-solid preparations that have petroleum jelly or their derivatives as a base. Petroleum jelly is a semi-solid mixture of hydrocarbons. As described in *Remington: The Science and Practice of Pharmacy,* 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid. An ointment may contain solid or encapsulated particles of a dry *Boswellia* or *Thymus* aqueous-ethanol extract or may contain an emulsified or suspended *Boswellia* or *Thymus* aqueous-ethanol extract.

Pastes. Pastes included herein contain, in addition to an ointment or cream base, high amounts of pulverulent constituents, such as zinc oxide, talc, starch or titanium dioxide. In one embodiment, the paste is selected from the group comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds. A paste may contain solid or encapsulated particles of a dry *Boswellia* or *Thymus* aqueous-ethanol extract or may contain an emulsified or suspended *Boswellia* or *Thymus* aqueous-ethanol extract.

Aerosols. Aerosol as provided herein includes products packaged under pressure and contain ingredients that are released upon activation of an appropriate valve system. Aerosols include all self-contained pressurized products, such as fine mists of spray or foam, that are emitted from a pressurized container containing a propellant, foams, or semisolid liquids. They may also be emitted by an unpressurized atomizer that is pressurized by a hand-operated pump rather than by stored propellant. In one embodiment, the aerosol comprises a container, a propellant, a concentrate containing an active ingredient, a valve (which may be a metered valve), and an actuator. The nature of these components determines characteristics such as delivery rate, foam density, and fluid viscosity. In another embodiment, the aerosol is a two-phase formulation comprising a gas and liquid. In another embodiment, the aerosol is a three-phase formulation comprising a gas, liquid, and suspension or emulsion of active ingredients. In this formulation, suitable excipients, such as wetting agents and/or solid carriers such as talc or colloidal silicas are included. In another embodiment, the propellant is liquefied or vaporized. In another embodiment, a solvent can be the propellant or a mixture of the propellant and co-solvents such as alcohol and polyethylene glycols. In another embodiment, the propellant is selected from the group comprising a spray, foam, or quick-breaking foam. In another embodiment, spray formulations are aqueous solutions in a container having a spray means, such as an atomizer or nebulizer. A spray may contain an aerosol of solid or encapsulated particles of a dry *Boswellia* or *Thymus* aqueous-ethanol extract composition or may contain a *Boswellia* or *Thymus* aqueous-ethanol extract in an atomized or aerosol liquid form.

A composition according to the invention may also be atomized or aerosolized for dispersement within a space, such as in a hospital or a room in which a patient recovering from pneumonia is housed. Methods for dispersement of such compositions are described by and incorporated by reference to Schur, U.S. Pat. No. 7,638,114.

Foams. In some embodiments, a *Boswellia* or *Thymus* aqueous-ethanol extract is delivered to the body while in a foam state, such as stable foam, for example, that is produced with or without a propellant. For example, the extract may be contained in a shaving foam and used for preventing bacterial infection of nicks, cuts or abrasions associated with shaving. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam. Active ingredients in a foam may be dispensed for subsequent placement on a dry wipe, a pre-moistened wipe, or other soft, flexible applicator (e.g., an object about 3-fingers wide or 4 to 10 cm wide) or other object to be used for application of the foam-based composition to the skin. The foam can be a non-propellant foam. A foam with a suitable stiffness of yield stress can be applied to the skin in any manner for sustained adherence and contact with the body. Examples of foam-based systems are described in U.S. Pat. No. 6,818,204, "Stable Foam for Use in Disposable Wipe," issued to Lapidus on Nov. 16, 2004, herein incorporated by reference. The Lapidus patent involves the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™, anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, the surfactant is present in an amount from about 2% to about 35% by weight, or from about 5% to about 15% by weight.

At least one foam stabilizing agent may be present in some foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%. In the Lapidus patent (U.S. Pat. No. 6,818,204), alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%.

A foam may be produced using the F2 Finger Pump Foamer™ manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein. Details of exemplary propellantless defoamers are described in U.S. Pat. No. 5,443,569, issued on Aug. 22, 1995, and U.S. Pat. No. 5,813,576, issued Sep. 29, 1998, herein incorporated by reference.

Other Elements in Topical Formulations. The topical formulations provided herein can include additional ingredients to affect the physical or functional characteristics of the formulations. Stabilizers, preservatives, humectants, regreasing agents, solvents or auxiliaries can be included to improve efficacy and dermal penetration. Dermal penetration-enhancing compounds provided have low toxicity to the skin and can promote percutaneous and oral mucosal absorption. In one embodiment, dermal penetration-enhancing compounds include propylene glycol, polyethylene glycol, dimethylsulphoxide, decylmethylsulphoxide, azones, N-methylpyrrolidone, diethyltoluamide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants. Viscosity enhancers or thickeners can be included. Such enhancers can prevent the formulation from spreading beyond the site of application. In one embodiment, Balsam Fir is a pharmaceutically acceptable viscosity enhancer. Another benefit of increasing the viscosity of the formulation is provided below in the section discussing thixotropic agents. Thickeners include suitable polymers such as carbomer, hydroxypropyl methylcellulose, hydroxyethylcellulose, PVM/MA decadiene cross-polymer and acrylates. Two or more thickeners can be added.

Spreading oils or emollients can be included. One benefit for including such oils is for better distribution on surfaces, in particular on the skin. Spreading oils are understood as those oily liquids which are distributed particularly easily on the skin. They are known as such in cosmetics. The following compounds are suitable spreading agents: silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parabens, pH adjusting agents, surfactants, chelators, such as disodium EDTA or sodium citrate, tackifying agents, fragrances and other compounds.

Other compounds that can be included in the topical formulation include other antimicrobial, antibacterial, anti-inflammatory ingredients, or other functional ingredients such as protectants from UV. These include, but not limited to, antibiotics that target Gram-negative or Gram-positive bacterial, antifungal compounds, NSAIDS, glucocorticoids (e.g., hydrocortisone and derivatives having the same core ring structure), benzyl alcohol, other botanical extracts or oils, such as those described herein.

The compositions of this invention may be used in conjunction with other active ingredients, such as phytochemicals or non-*Boswellia* or *Thymus* extracts, bacteriostatic agents, bactericidal agents, antibiotics, antiseptics, or anti-inflammatory agents.

Encapsulation. The *Boswellia* or *Thymus* extracts described herein can be encapsulated in a carrier such as in liposomes, micelles, or microspheres. Suitable carriers are described in U.S. Pat. No. 7,205,003, hereby incorporated by reference.

Micelles. Micelles provided herein can comprise surfactant molecules arranged such that their polar head groups form an outer spherical shell, while their hydrophobic, hydrocarbon chains are oriented towards the center of the sphere, forming a core. The precursor and agent are encapsulated within the core of the micelle. Surfactants suitable for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Liposomes. Liposomes provided herein are microscopic vesicles having a lipid wall comprising a lipid bilayer. Liposomal preparations herein include cationic (positively charged), anionic (negatively charged), and neutral preparations. Cationic liposomes include N[1-2,3-dioleyloxy)propyl]-N,N,N-triethylammonium (DOTMA). Anionic and neutral liposomes can be easily prepared using materials such as phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE). These materials can also be mixed with DOTMA in appropriate ratios.

Microspheres. Microspheres provided herein can comprise micro- or nano-scale carriers that are made of polymers, both synthetic and natural. Additional nomenclature describing microspheres include, but are not limited to, spheres, beads, particles, carriers, microbeads, microparticles, microcarriers, nanospheres, nanobeads, nanoparticles, and nanocarriers.

Polymeric materials suitable for the microspheres provided herein include those that are described in U.S. Pat. No. 6,423,345, hereby incorporated by reference in its entirety for all purposes, including poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Natural polymers including agarose and alginate are also suitable for the microspheres. Any of the above carriers can include proteins, lectins, and other biological materials. The precursors and activating agents can be encapsulated into the carriers using known techniques in the art, including microspheres described in U.S. Pat. No. 6,423,345, incorporated by reference, including solvent evaporation, hot melt microencapsulation, solvent removal, and spray drying of microspheres. In one embodiment, the microsphere comprises a block copolymer. In another embodiment, the microsphere comprises a hydrogel.

Suppositories. In addition to the active *Boswellia* or *Thymus* extract, a suppository may contain the customary water-soluble or water-insoluble excipients, for example polyethylene glycols, fats, for example cocoa fat and higher esters (e.g., $C_{14}$-alcohol with $C_{16}$-fatty acid) or mixtures of these substances.

Tablets, Capsules, Pills. In some embodiments, the *Boswellia* or *Thymus* aqueous-ethanol extract will be formulated as a tablet, capsule or pill that contains a *Boswellia* or *Thymus* aqueous-ethanol extract. These may contain the customary excipients, such as fillers and extenders, for example starches, lactose, sucrose, glucose, mannitol, and silicic acid; binders, for example carboxymethyl cellulose, alginates, gelatin, polyvinylpyrrolidone; humectants, for example glycerin; disintegrating agents, for example agar-agar, calcium carbonate and sodium carbonate; dissolution retardants, for example paraffin; resorption accelerating agents, for example quaternary ammonium compounds; wetting agents, for example cetyl alcohol, glycerol monostearate; adsorption agents, for example kaolin and bentonite; and lubricants, for example talcum, calcium stearate and magnesium stearate, and solid polyethylene glycols or mixtures of the substances mentioned above. In some embodiments, the active ingredient(s) can be in a microencapsulated form in the tablet or capsule, which can optionally be formulated to release the active *Boswellia* or *Thymus* component at a particular location within the GI tract, e.g, to transit the stomach and release the active component in the small or large intestine.

Powder. A composition according to the invention may be formulated in the form of an antimicrobial powder which contains a dry or encapsulated *Boswellia* or *Thymus* extract and the customary excipients, for example lactose, talcum, silicic acid, aluminum hydroxide, calcium silicate, and polyamide powder, or mixtures of these substances. Such powders may be formulated for topical application or for inhalation.

Deodorant/Personal Care. The compositions of the invention can be formulated as deodorants or personal care products that prevent the formation of body odors such as those produced by the growth of Gram-positive bacteria in or on the skin. Such deodorant will contain an antimicrobial amount of the *Boswellia* or *Thymus* extract and suitable excipients or carriers to facilitate its application to the body. *Boswellia* or *Thymus* extract may be incorporated into conventional body washes, lotions, lubricants, personal care composition, antiperspirants, or deodorants. Such products are well known in the art and commercially available and are also described by Broad, U.S. Pat. No. 4,252,789, which is incorporated by reference, especially for their descriptions of conventional deodorant ingredients, formulations, and modes of use. These products can be applied to the axilla, inguinal region, feet or other odor-producing body part to prevent growth of odor-causing microorganisms. In other embodiments, the extract of the invention can be incorporated into a deodorizer, cleaner, or disinfectant such as a liquid sanitizer or disinfectant, a spray or wipe for cleaning surfaces exposed to bacterial contaminants.

Cleaning Agent. A composition containing a *Boswellia* or *Thymus* aqueous-ethanol extract may be formulated for use as a cleaning or disinfecting agent, such as a hard surface cleaning product. It may further contain cleaning agents, such as chelators or surfactants, which do not interfere with the antimicrobial activity of the *Boswellia* or *Thymus* extract. The formulation of such a cleaning or disinfecting solution and inclusion of general cleaning agents can easily be done by a skilled artisan and the stability and effectiveness of the solution can be easily tested by the skilled artisan. The term "hard surface cleaning composition" refers to a composition that is used to clean and/or sanitize a hard or solid surface. In one embodiment, the invention provides a composition that prevents bacterial growth on hard surfaces including, but not limited to, surgical instruments, storage tanks, pipelines, trays, containers, walls, floors, countertops, locker room floors, benches, lockers, showers, bathrooms, toilets, water filtration units, and the like.

Foods, Beverages & Feeds. In other embodiments, the formulation is in the form of an ingestible food or beverage or in an additive or protectant in aquaculture. It may be a human food or animal feed that contains a *Boswellia* or *Thymus* aqueous-ethanol extract. Such extracts may be incorporated into animal feeds for mammals (cattle, sheep, goats, etc.), birds (e.g., chickens, turkeys, quail, ducks, geese, hawks, falcons, etc.), fish (e.g., tilapia, carp, catfish, salmon, trout, aqua cultured fish, etc.), and crustaceans (e.g., shrimp, lobsters, etc.), mollusks (e.g., abalone, oysters, clams, mussels, etc.). In some embodiments, the *Boswellia* or *Thymus* extract of the invention will be incorporated into a liquid medium in which an animal is grown, e.g., into a medium for aquaculture. In other embodiments, the extract may be encapsulated in a form that permits uptake by an animal, for example, in an encapsulated particulate form that can be ingested by fish.

Plants. In some embodiments, the *Boswellia* or *Thymus* extract of the invention can be applied to control the growth of Gram positive bacteria in or on plants, such those causing leaf spots, rots, scabs, and wilting. It may be sprayed or otherwise applied to the roots, foliage, flowers or seeds of a plant. It may be added to culture medium used for hydroponic cultivation of plants.

In many embodiments, the *Boswellia* or *Thymus* aqueous-ethanol extract will exert antimicrobial activity on anti-Gram positive bacteria. Antimicrobial activity may be determined or quantified by assays known in the art. Representative assays are described below.

An appropriate content of *Boswellia* or *Thymus* and one or more other herbal extracts may be selected based on the antimicrobial activity or healing properties of the mixtures. In some embodiments the ratio of *Boswellia* or *Thymus* aqueous-ethanol extract to another herbal extract will range from 0.1 to 100 to 100 to 0.1 as well as any endpoint or intermediate ratio. Such ratios include 50:1, 20:1, 10:1, 5:1, 2:1, 1:1, 1:2, 1:5, 1:10, 1:20, and 1:50 and may be based on the weight on anhydrous or solid components of the extracts, and these ratios also describe mixtures of a *Boswellia* aqueous-ethanol extract with a *Thymus* aqueous-ethanol extract.

By an "effective" amount or a "therapeutically effective" amount of the *Boswellia* or *Thymus* aqueous-ethanol extract is meant a nontoxic but sufficient amount of the extract to provide a beneficial effect, such as an antimicrobial, regenerative, or healing effect. The amount of active agent that is "effective" will vary from subject to subject, depending on the age and general condition of the individual, the particular active agent or agents, and the like. It may also depend on the microorganism or condition being treated. Unless otherwise indicated, the term "therapeutically effective" amount as used herein is intended to encompass an amount effective for the prevention, the amelioration of a microbial infection and/or treatment of an adverse condition, such as wounds, damage to skin, or damage to a mucous membrane or tissue of the respiratory system. Determination of a therapeutic effect may be made by comparison with an otherwise identical composition that does not contain the *Boswellia* or *Thymus* aqueous-ethanol extract, or which contains a control extract from a different source, such as a similar amount of a similar aqueous-ethanol extract of a different plant.

The terms "treating" and "treatment" as used herein refer to the administration of a composition containing a *Boswellia* or *Thymus* aqueous-ethanol extract to a clinically symptomatic individual afflicted with an adverse condition, disorder, or disease, such as pneumonia, so as to effect a reduction in severity and/or frequency of symptoms, eliminate the symptoms and/or their underlying cause, and/or facilitate improvement or remediation of damage. Analogously, this term also applies to treatment of objects, such as contacting an extract with a surgical surface or with surgical tools or equipment to kill, inhibit or remove microbial contaminants.

The terms "preventing" and "prevention" refer to the administration of an extract or composition to a clinically asymptomatic individual who is susceptible to a particular adverse condition, disorder, or disease, and thus relates to the prevention of the occurrence of symptoms and/or their underlying cause. For example, treatment may decrease the susceptibility of an individual at risk of developing pneumonia to pneumonia, or reduce the number of gram-positive bacteria or gram-negative bacteria in a wound, reduce inflammation, accelerate wound healing, accelerate healing of a mucous membrane or respiratory tissue, or prevent or ameliorate scar formation. Analogously, this term also applies to prevention of microbial, especially bacterial, contamination of objects, such as contacting an extract with a surface or surgical equipment to prevent or remove microbial contamination.

In some embodiments, treatment or prevention may be individualized for treatment of a particular kind of subject, or for treatment of a particular disease, disorder or condition, for example, for treatment of pneumonia caused by a particular isolate of *S. pneumoniae* or individualized for treatment of subjects exposed to a particular clinical isolate. Such an individualized treatment method will generally be performed in conjunction with identification of the particular kind of subject or particular disease, disorder or condition to be treated.

In other embodiments, a *Boswellia* or *Thymus* extract or composition containing it may be administered with or in conjunction with one or more antibiotics to enhance, add to, or synergize the antimicrobial effect of the antibiotic, especially, an antibiotic to which multiple drug resistance has developed. Antibiotics include, but are not limited to, those commonly used to treat pneumonia such as penicillins, macrolides, clindamycin, cephalosporins, rifampin, vancomycin, and trimethoprim-sulfamethoxazole.

Respiratory pathogens include but are not limited to *Streptococcus pneumoniae* (a gram-positive bacterium), *Klebsiella pneumoniae* (a gram-negative bacterium) and *Mycoplasma pneumoniae*. Other respiratory pathogens include those described in Table 93-1, "Common Agents of Respiratory Infections" (incorporated by reference) available at: hypertext transfer protocol://_www.ncbi.nlm.nih-.gov/books/NBK8142/table/A4991/?report=object only (last accessed Sep. 27, 2017). Pathogens associated with wounds such as musculoskeletal wounds include *Staphylococcus aureus, Staphylococcus epidermidis*, and *Pseudomonas aeruginosa.*

The following embodiments illustrate various aspects of the present invention. They are not to be construed to limit other aspects of the invention in any manner.

Other embodiments include the following:

Embodiment 1. A method for treating a microbial disease, disorder, or condition comprising:

extracting a *Boswellia* gum-resin with an aqueous-ethanol solution containing 35-65 wt % water and 65-35 wt % ethanol, removing water and ethanol to produce a concentrated or dessicated extract, and administering a composition containing an effective amount of the concentrated or dessicated extract to a subject in need thereof. In an alternative embodiment, an aqueous-ethanol extract of *Thymus* leaves may be prepared (in place of a *Boswellia* gum-resin) as described above and administered to a subject in need thereof. In yet other embodiments, both a *Boswellia* and *Thymus* extract may be prepared and administered. Ranges described in the following embodiments include all intermediate subranges and values.

Embodiment 2. The method of Embodiment 1, wherein said microbial disease, disorder, or condition is pneumonia.

Embodiment 3. The method of Embodiment 1, wherein said microbial disease, disorder, or condition is caused by *Streptococcus pneumoniae*.

Embodiment 4. The method of Embodiment 1, wherein said microbial disease, disorder, or condition is caused by *Klebsiella pneumoniae*.

Embodiment 5. The method of Embodiment 1, wherein said microbial disease, disorder, or condition is a wound, inflammation, or other disorder of skin, a mucous membrane, or respiratory system tissue.

Embodiment 6. The method of Embodiment 1, wherein the *Boswellia* extract is produced by grinding, comminuting, pulverizing, or otherwise dissolving or suspending *Boswellia* gum-resin in an aqueous-ethanol solution containing 35-65 wt % water and 65-35 wt % ethanol;

mixing the ground, comminuted, pulverized, or otherwise dissolved or suspended *Boswellia* resin with water and/or ethanol for a time sufficient to extract water and/or alcohol soluble components, and separating solid or other insoluble components from the mixture, thereby providing said extract.

Embodiment 7. A method for producing an aqueous-ethanol extract of *Boswellia* comprising: grinding, comminuting, pulverizing, or otherwise dissolving or suspending *Boswellia* gum-resin in an aqueous-ethanol solution containing 35-65 wt % water and 65-35 wt % ethanol;

mixing the ground, comminuted, pulverized, or otherwise dissolved or suspended *Boswellia* resin with water and/or ethanol for a time sufficient to extract water and/or alcohol soluble components, and separating solid or other insoluble components from the mixture, thereby providing said extract.

Embodiment 8. The method of Embodiment 7 that comprises extracting the *Boswellia* gum-resin with a solution of 45-55 wt % water and 55-45 wt % ethanol.

Embodiment 9. The method of Embodiment 7 that comprises extracting the *Boswellia* gum-resin with a solution of about 50 wt % water and about 50 wt % ethanol.

Embodiment 10. The method of Embodiment 7, wherein the mixing is performed at a pH ranging from 5.0 to 9.0 and at a temperature ranging from >0° C. to 100° C.

Embodiment 11. The method of Embodiment 7, wherein the mixing is performed at a pH ranging from 6.0 to 8.0 and at a temperature ranging from 15° C. to 30° C.

Embodiment 12. The method of Embodiment 7, further comprising removing substantially all water and ethanol from said extract to produce an extract substantially free of water and ethanol.

Embodiment 13. The method of Embodiment 12, further comprising admixing said extract substantially free of water and ethanol with at least one pharmaceutically acceptable excipient, solvent, or carrier to produce a composition.

Embodiment 14. The composition produced by the method of Embodiment 13 that contains the extract that is substantially free of water and ethanol in an amount ranging from 0.001 to <100 wt %, wherein the wt % of the extract is based on weight of the extract not taking into account weight of any water and ethanol.

Embodiment 15. The composition of Embodiment 14 in the form of solution.

Embodiment 16. The composition of Embodiment 14 in the form of an oil-in-water or water-in-oil emulsion.

Embodiment 17. The composition of Embodiment 14 in the form of a serum, gel, lotion or cream.

Embodiment 18. The composition of Embodiment 14 in the form of a spray, aerosol, mist, or foam.

Embodiment 19. The composition of Embodiment 14 in the form of a bandage, compress, dressing, tamponade, gauze, diaper, wipe, deodorant, lubricant, or personal care product.

Embodiment 20. An aqueous-ethanol extract of *Boswellia* gum-resin from which insoluble components have been removed, wherein said *Boswellia* gum-resin has been extracted with a solution of 35-65 wt % water and 65-35 wt % ethanol.

Embodiment 21. An aqueous-ethanol extract of *Boswellia* gum from which insoluble components have been removed, wherein said *Boswellia* gum has been extracted with a solution of about 35-65 wt % water and about 65-35 wt % ethanol; or an aqueous-ethanol extract of *Thymus* leaves from which insoluble components have been removed, wherein said *Thymus* leaves have been extracted with a solution of about 35-65 wt % water and about 65-35 wt % ethanol. These ranges include all intermediate values and subranges.

Embodiment 22. The aqueous-ethanol extract of Embodiment 21, wherein the *Boswellia* gum-resin or *Thymus* leaves have been extracted with a solution of about 45-55 wt % water and about 55-40 wt % ethanol.

Embodiment 23. The aqueous-ethanol extract of Embodiment 21, wherein the *Boswellia* gum-resin or *Thymus* leaves have been extracted with a solution of about 50 wt % water and about 50 wt % ethanol.

Embodiment 24. The aqueous-ethanol extract of Embodiment 21 that consists essentially of soluble components extracted from *Boswellia* gum-resin or that consists essentially of soluble components extracted from *Thymus* leaves.

Embodiment 25. The aqueous-ethanol extract of Embodiment 21 that has had substantially all ethanol removed from it.

Embodiment 26. The aqueous-ethanol extract of Embodiment 21 that has had substantially all ethanol and all water removed from it.

Embodiment 27. The extract of Embodiment 21 that is produced by:

grinding, comminuting, pulverizing, or otherwise dissolving or suspending *Boswellia* gum-resin or *Thymus* leaves in a solution containing water and/or ethanol;

mixing the ground, comminuted, pulverized, or otherwise dissolved or suspended *Boswellia* resin and/or *Thymus* leaves with water and/or ethanol for a time sufficient to extract water and/or alcohol soluble components, and separating solid or other insoluble components from the mixture, thereby providing said extract.

Embodiment 28. The extract of Embodiment 27, wherein the mixing is performed at a pH ranging from about 5.0 to 9.0 and at a temperature ranging from >0° C. to 100° C. These ranges include all intermediate values and subranges.

Embodiment 29. The extract of Embodiment 27, wherein the mixing is performed at a pH ranging from 6.0 to 8.0 and at a temperature ranging from 15° C. to 30° C.

Embodiment 30. A composition comprising the extract of Embodiment 21 in an amount ranging from 0.001 to 100 wt %, wherein the wt % of the extract is based on weight of the extract once ethanol and water have been removed. This range includes all intermediate values and subranges.

Embodiment 31. The composition of Embodiment 30 in the form of solution.

Embodiment 32. The composition of Embodiment 30 in the form of an oil-in-water or water-in-oil emulsion.

Embodiment 33

The composition of Embodiment 30 in the form of a serum, gel, lotion or cream.

Embodiment 34. The composition of Embodiment 30 in the form of a spray, aerosol, mist, or foam.

Embodiment 35. The composition of Embodiment 30 in the form of a bandage, compress, dressing, tamponade, gauze, diaper or wipe.

Embodiment 36. The composition of Embodiment 30 in the form of a deodorant, lubricant, or personal care product.

Embodiment 37. A method for treating a microbial disease, disorder, or condition comprising administering a composition comprising the *Boswellia* extract and/or *Thymus* extract of Embodiment 21 to a subject in need thereof.

Embodiment 38. The method of Embodiment 37, wherein the subject is infected with or harbors *Streptococcus pneumoniae* in the respiratory system.

Embodiment 39. A method for treating a wound or injury comprising contacting it with the composition of Embodiment 30.

Embodiment 40. The method of Embodiment 39, wherein the wound or injury is to skin or to a mucous membrane. In some embodiments, the wound or injury will be one exposed or contaminated with bacteria, such as those causing pneumonia like *S. pneumoniae, K. pneumoniae*, or *M. pneumoniae*.

EXAMPLES

The following examples describe certain aspects of the present invention. They are not to be construed to limit the invention in any manner.

The antimicrobial activity of aqueous-ethanol extracts of *Boswellia* and/or *Thymus* was evaluated against clinical isolates of *S. pneumoniae* and *Klebsiella pneumoniae*. Extracts of *Boswellia* resin and *Thymus* leaves were prepared using ethanol and water (1:1). Antimicrobial activity was measured by zone inhibition and by determination of the minimal inhibition concentration ("MIC") of the extracts as shown in Tables 1 and 2. HPLC was used to analyze the components of these extracts as shown in Tables 3 and 4.

Example 1

Production of *Boswellia* and *Thymus* Extracts

Leaves of *Thymus domesticus* and gums of *Boswellia serrata* were collected from local markets in Dammam, Saudi Arabia, and then were dried and ground into powder.

A weight of 30 gr of ground Thyme leaves or 30 gr of powdered *Boswellia* gum-resin were suspended in either (i) 100 ml of distilled water, (ii) 100 ml of 95 wt % ethanol, or (iii) 100 ml of a 1:1 mixture of distilled water and 95 wt % ethanol for a period of three days at room temperature.

Solids were then separated from the liquid fraction by filtration through a 0.45 or 0.22 micron filter.

The liquid fractions (extracts) were subjected to rotary evaporation at 60° C. for 24 hrs to remove ethanol and water by evaporation to recover non-water and non-ethanol components of the extraction as a residuum or crude dry extract.

The recovered material was resuspended to pre-specified concentrations in suitable solvents for analysis of its components and determination of its antimicrobial properties.

Example 2

Evaluation of Antimicrobial Properties of Thyme and *Boswellia* Extracts

The effects of contacting several different kinds of bacteria with the Thyme and *Boswellia* extracts were evaluated.

Standard strains of *Streptococcus pneumoniae* ATCC 49619 and *Klebsiella pneumoniae* ATCC 7006003 were used. Standard strains of *E. coli* ATCC 25922, *Staphylococcus aureus* and *Pseudomonas aeruginosa* strains ATCC 25923 and ATCC 27853 were obtained from Laboratory of Microbiology of King Fahad hospital in Khobar city. Twenty clinical isolates of *Streptococcus pneumoniae* and five clinical isolates of *Klebsiella pneumoniae* were isolated from different patients.

The well diffusion assay technique was used to evaluate antibacterial effects of each extract. An amount of 0.1 ml of an overnight bacterial culture strain was inoculated into trypticose soy broth. Overnight culture inoculum was spread over blood agar by using L-shape spreader and sterile swaps. Holes were made by using sterile 5 mm diameter cork porer. Plates were then incubated at 37° C. for 24 h. sterile water and solvents were used as controls and 1:1 combination of *Thymus* and *Boswellia* extracts was used The diameter of the inhibition zone was estimated in mm.

Minimum Inhibitory Concentration Assay (MIC)

Bacterial isolates showed susceptibility to the extracts, their antibacterial response was determined using extracts at dilutions 0.25, 0.5, 0.75 µl/ml (microliter of crude dry extract/ml solvent) and sterile solvent as control treatment. Minimum inhibitory concentration (MIC) was determined as described by Sienkiewicz, M. et al. "The Antimicrobial Activity of Thyme Essential AZ Oil Against Multidrug Resistant Clinical Bacterial Strains", MICROBIAL DRUG RESISTANCE, Vol. 18, No. 2, 2012, pages 137-148 (incorporated by reference), and was read in u/ml after overnight incubation at 37° C. All experiments were made in replicate.

TABLE 1

| Solvent | Ethanol 96% | $H_2O$ | Ethanol: $H_2O$ |
|---|---|---|---|
| *Thymus* extract × *S. pneumoniae* | 4 | 3 | 15 |
| *Thymus* extract × *K. pneumoniae* | 3.2 | 2 | 7 |
| *Boswellia* extract × *S. pneumoniae* | 9 | 34 | 30 |
| *Boswellia* × *K. pneumoniae* | 5 | 0 Resistant (R) | 8 |

A larger number in the table above indicates a greater zone of bacterial growth inhibition and a greater antimicrobial effect. Results presented in Table 1 indicate that

*Thymus* and *Boswellia* extracted with a water: ethanol mixture (1:1) gave the highest antibacterial effect against both *S. pneumoniae* and *K. pneumoniae* as measured by diameter of inhibition zone. These results show that extraction with a mixture of ethanol and water produces an extract with higher anti-bacterial properties than extraction with 96% ethanol alone or by extraction with water alone. Results show that the application of aqueous and alcohol extracts of *Thymus* and *Boswellia* gave high inhibitory action compared to aqueous extracts. While not being bound to any particular explanation, this could be related to increased inhibitor concentrations in the aqueous-ethanol extract not obtained by the other extraction methods.

Extracts of *Thymus* and *Boswellia* were tested against standard and clinical isolates of bacteria causing pneumonia. The minimal inhibitory concentration (MIC) of *Boswellia* and *Thymus* extracts and the diameters of inhibition zones ("I.Z.") produced by *Boswellia, Thymus*, or a 1:1 mixture of *Boswellia+Thymus* extracts on various bacteria isolates were determined substantially as described above. MIC is defined as the lowest concentration that will inhibit the growth of test bacteria after 18-24 hr (Javed et al. "In vitro Evaluation of the Synergistic Antimicrobial Effect of *Boswellia sacra* and *Nigella sativa*, Essential Oil on Human Pathogenic Microbial Strains", AMERICAN JOURNAL OF PHYTOMEDICINE AND CLINICAL THERAPEUTICS, Vol. 3, No. 2, 2015, pages 185-192, incorporated by reference).

The amounts described below using the concentration unit "µl/ml" refer to the number of microliters of each crude dry extract (after removal of water and ethanol) added to each ml of test solution.

TABLE 2

Antibacterial effect of *Boswellia* and *Thymus* extracts on *pneumoniae* isolates by disk diffusion and MIC method.

| Isolates *S. pneumoniae* ("S.p.") or *K. pneumoniae* ("K.p.") | *Boswellia* extract LZ (mm) | *Boswellia* extract MIC (µl/ml) | *Thymes* extract LZ (mm) | *Thymes* extract MIC (µl/ml) | Mixed *Boswellia* and *Thymus* Extracts LZ (mm) |
|---|---|---|---|---|---|
| S.p. (ATCC) | 30 | 0.25 | 15 | 0.75 | R |
| K.p. (ATCC) | 8 | 0.75 | 7 | 0.75 | R |
| S.p.1 | R | — | R | — | R |
| S.p.2 | R | — | R | — | R |
| S.p.3 | 4 | 0.75 | R | — | R |
| S.p.4 | 8 | 0.25 | R | — | 16 |
| S.p.5 | 12 | 0.50 | R | — | R |
| S.p.6 | 2 | 0.50 | R | — | R |
| S.p.7 | R | — | 4 | 0.25 | 3 |
| S.p.8 | 22 | 0.25 | 3 | 0.25 | 17 |
| S.p.9 | 19 | 0.25 | 3 | 0.25 | 2 |
| S.p.10 | R | — | 1 | 0.50 | 3 |
| S.p.11 | 4 | 0.75 | 3 | 0.75 | R |
| S.p.12 | R | — | R | — | R |
| S.p.13 | 11 | 0.50 | R | — | R |
| S.p.14 | 1 | 0.75 | R | — | R |
| S.p.15 | 4 | 0.50 | 12 | 0.75 | R |
| S.p.16 | 5 | 0.50 | R | — | R |
| S.p.17 | R | — | R | — | R |
| S.p.18 | 7 | 0.25 | R | — | 2 |
| S.p.19 | R | — | R | — | R |
| S.p.20 | R | — | R | — | R |
| K.p.1 | R | — | R | — | R |
| K.p.2 | R | — | R | — | R |
| K.p.3 | 12 | 0.75 | R | — | R |
| K.p.4 | R | — | R | — | R |
| K.p.5 | R | — | R | — | R |

*I:Z: Inhibition zone by mm., *S.p. = *Streptococcus pneumoniae*., *K.p. = *Klebsiella pneumoniae*., *MIC = Minimum inhibitory concentration (µl/ml)., *B:T = *Boswellia* and *Thymus* (1:1) mixed extract.
The mixed extract contained the same concentrations of the *Boswellia* and *Thymus* extracts as were tested for each individual extract.

Table 2 shows the results of antibacterial activity of *Boswellia* and *Thymus* extracts on *pneumoniae* isolates using disk diffusion and the MIC.

*Streptococcus pneumoniae* (ATCC) was used as a control isolate and was more sensitive to *Boswellia* extracts than the *Klebsiella pneumoniae* (ATCC) reference strain. *Klebsiella pneumoniae* (ATCC) gave 8 mm and 7 mm zones of inhibition with *Boswellia* and thyme extracts, respectively.

Results indicated that inhibition zones ranged from 2-30 mm, twelve *S. pneumoniae* isolates were sensitive to *Boswellia* extracts, which equals 60% of the tested isolates. MIC of four *S. pneumoniae* isolates was 0.75 µ/ml, and 5 isolates have 0.5 µ/ml MIC. 30% from the tested bacterial isolates were resistant to *Boswellia* extract. However, 6 isolates of *S. pneumoniae* (representing 30% of isolates) were sensitive to the *Thymus* extract and the rest were resistant. Inhibition zones of *S. pneumoniae* isolates were ranging from 1-12 mm, and MIC values of the sensitive isolates were 0.25 µ/ml for 3 isolates and were 0.75 µ/ml for 2 isolates, and one isolate has 0.5 µ/ml MIC.

Table 2 shows that six *S. pneumoniae* isolates (30% of isolates) were sensitive to *Boswellia* and *Thymus* (1:1) mixed extract, and gave inhibition zones that ranged from 2-7 mm, Isolates No. 4 and 8 were more sensitive to *Boswellia* extracts, but the rest of tested isolates were resistant. No effect of the *Thymus* extract on any of *K. pneumoniae* clinical isolates was observed. These results show that *Boswellia* extract generally exhibited a higher antimicrobial activity than Thyme extract on the tested isolates. While not being bound to any particular explanation, at least one component of the inhibitory effect of extracts for *Boswellia* and *Thymus* may correlate with their hydrophobicity. A more hydrophobic extract could more efficiently partition the membrane lipids of the bacterial cell, make them more permeable, increase transmembrane leakage, and subsequently lead to death of the bacterial cell. Resistance of gram-negative bacteria, such as *Klebsiella* might be attributed to its hydrophilic outer membrane containing lipopolysaccharide (LPS) which may act as penetration barrier for macromolecules and hydrophobic compounds contained in a *Boswellia* or *Thymus* extract. Many *K. pneumoniae* and *S. pneumoniae* strains were resistant against mixed extracts of *Boswellia* and thyme. For such strains, an antimicrobial extract or composition containing an extract may contain only a *Boswellia* extract or a *Thymus* extract, but not both. Similarly, such strains may be treated with compositions exclusively containing an extract of *Boswellia* or *Thymus*, but not other herb- or plant-based extracts.

Chemical Analysis of Extracts

Chemical analyses of the *Boswellia* and *Thymus* extracts were performed using (HPLC) chromatography, Agilent device (1100HPLC). Phenolic compounds were estimated at 280 nm wavelength, and flavonoid carried out under the following conditions, degazer auto-sampler, quaternary pump and column cabin was at 35° C. and the fragmentation column was zorbox ODS of 5 μm 4.6×250 mm dimensions. The flow rate of the mobile phase was 1 ml/min as described by Pascale GOUPY, et al., "Antioxidant composition and activity of barley (*Hordeum vulgare*) and malt extracts and of isolated phenolic compounds", JOURNAL OF THE SCIENCE OF FOOD AND AGRICULTURE, Vol. 79. 1999. pages 1625-1634 and Pirjoet MATTILA, et al., "Determination of Flavonoids in Plant Material by HPLC with Diode-Array and Electro-Array Detections", J. AGRIC. FOOD CHEM., Vol. 48. No. 12, 2000, pages 5834-5841, both of which are incorporated by reference. The results of these analyses are shown in Tables 3 and 4.

TABLE 3

Thyme and frankincense flavonoids concentrations (ppm) using HPLC.

| Flavonoids | Test results of flavonoids (ppm) Thyme | *Boswellia* |
|---|---|---|
| Luteolin | — | 4.1888 |
| Narengin | 975.92 | 7.55 |
| Rutin | 118.2 | 3.3873 |
| Hisperidin | 1418.6 | 10.847 |
| Rosmarinic | 604.07 | 5.3906 |
| Quercetrin | 92.229 | 1.2138 |
| Quercetin | 53.745 | 5.7968 |
| Hispertin | 38.467 | 12.058 |
| Kampferol | 175.63 | 1.8054 |
| Apegnin | 101.09 | 1.5162 |
| 7-OH-hydroxyflavone | 115.63 | 1.8481 |
| Total | 3693.581 | 55.6012 |

TABLE 4

Thyme and frankincense phenolic compounds concentrations (ppm) using HPLC.

| Test results of phenolic compounds (ppm) *Boswellia* | Thyme | Phenolic compounds/ acids |
|---|---|---|
| 1.09 | 2.90 | Gallic |
| 33.09 | 177.87 | Pyrogallol |
| 0.51 | 6.30 | Amino-benzoic-4 |
| 1.12 | 3.74 | OH-Tyrosol-3 |
| 2.98 | 5.62 | Protocatchuic acid |
| 9.05 | 84.37 | Catechein |
| 3.16 | 36.10 | Chlorogenic |
| 10.22 | 105.50 | Catechol |
| 6.33 | 24.31 | Epicatechein |
| 2.87 | 55.12 | Caffeine |
| 4.67 | 70.33 | P—OH-benzoic |
| 4.56 | 71.49 | Caffeic |
| 8.21 | 84.61 | Vanillic |
| 6.51 | 17.76 | P-coumaric |
| 3.02 | 70.72 | Ferulic |
| 4.58 | 110.56 | Iso-ferulic |
| 2.68 | 15.65 | Resveratrol |
| 147.65 | 877.47 | e-vanillic |
| 49.91 | 164.71 | Ellagic |
| 16.82 | 56.93 | Alpha-coumaric |
| 102.94 | 254.32 | Benzoic |

TABLE 4-continued

Thyme and frankincense phenolic compounds concentrations (ppm) using HPLC.

| Test results of phenolic compounds (ppm) *Boswellia* | Thyme | Phenolic compounds/ acids |
|---|---|---|
| 14.26 | 16.25 | methoxy-cinnamic-3,4,5 |
| 6.04 | 34.83 | Coumarin |
| 21.42 | 61.45 | Salicylic acid |
| 4.04 | 24.80 | Cinnamic |
| 41.47 | 52.87 | Thymol |
| 509.2 | 2485.58 | Total |

Results of Tables 3 and 4 show the flavonoid and phenolic compounds concentrations in *Thymus* and *Boswellia* extracts using HPLC chemical analysis which describes various phenolic acids such as e-vanillic, caffeic, ellagic, etc. Results show that phenol and flavonoid concentrations in thyme are higher than in *Boswellia* extracts (2485.6 ppm and 509.2 ppm phenol content) and (3963.6 ppm and 55.6 ppm flavonoid), respectively.

Despite the higher concentrations of flavonoid and phenolic compounds in *Thymus* than those of *Boswellia* as shown by Tables 3 and 4, *Boswellia* showed higher antimicrobial activity than *Thymus*, except in case of *K. pneumoniae* where the opposite was observed.

As shown by the data above, extracts of both *Thymus* and *Boswellia* are effective antibacterial compositions, especially against clinical isolates of *Streptococcus pneumoniae* and *Klebsiella pneumoniae*.

*Boswellia* extract was more efficient than thyme extracts, 60% of *S. pneumoniae* isolates and one *K. pneumoniae* isolate were sensitive to *Boswellia* extract, while 30% of *S. pneumoniae* isolates were sensitive to thyme extract, no effect on *K. pneumoniae* clinical isolates was observed. Inhibition zones ranged from 1-12 mm with thyme extract, while *Boswellia* extracts showed 2-30 mm diameters of inhibition zone. In some embodiments, an antibacterial composition will contain *Boswellia* extract but no *Thymus* extract. In other embodiments, an antibacterial composition will contain *Boswellia* extract as well as a *Thymus* extract. In still other embodiments an antibacterial composition will contain a *Thymus* extract but no *Boswellia* extract.

Some embodiments of the invention a dry, or dessicated extract of *Boswellia* or *Thymus* will have about the same proportions of flavonoids and/or phenolic compounds as shown in Tables 3 and 4. In other embodiments, the amount of one or more flavonoid or phenolic compounds may vary downward or upward by about 0, 5, 10, 15 or 20% (or any intermediate value within this range) of the value described by Table 3 or 4.

Compositions containing two, three, four, five or more of the ingredients described in Tables 3 and 4 may also be produced by mixture of isolated ingredients (such as a purified flavonoid or phenolic compound) or by admixture of an aqueous-ethanol extract (e.g., in dry or dessicated form without substantial content of water or ethanol) of *Boswellia* or *Thymus* with a carrier or excipient, optionally with the addition of one, two, three, four, five or more isolated flavonoids and/or phenolic compounds or with flavonoids and/or phenolic compounds derived from other natural sources. In some embodiments, such compositions will contain 0.1, 0.25, 0.5, 1, 2, 5, 10, 25, 50, or 100 or more-times the concentration of a flavonoid and/or phenolic compound described in Table 3 or 4. This range includes all intermediate values.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by insertion of a space or underlined space before "www" and may be reactivated by removal of the space.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method of treating a skin wound containing *Klebsiella pneumoniae* in a subject in need of said treatment, comprising:

applying an ointment to the skin wound, wherein the ointment comprises an effective amount of an anti-microbial composition to inhibit growth of the *Klebsiella pneumoniae* in the skin wound, wherein the ointment contains semisolid hydrocarbons comprising a *Boswellia serrata* extract;

administering one or more antibiotics selected from the group consisting of a penicillin, a macrolide, a clindamycin, a cephalosporin, a rifampin, a vancomycin, and a trimethoprim-sulfamethoxazole in conjunction with the applying of the ointment to the skin wound;

wherein said anti-microbial composition comprises 4.188±10% ppm luteolin, 7.55±10% ppm narengin, 3.3873±10% ppm rutin, 10.847±10% ppm hisperidin, 5.3906±10% ppm rosmarinic, 1.2138±10% ppm quercetrin, 5.7968 quercetin, 12.058±10% ppm hispertin, 1.8054±10% ppm kampferol, 1.5162±10% ppm apegnin, and 1.8481±10% ppm 7-OH-hydroxyflavone; and/or 1.09±10% ppm gallic acid, 33.09±10% ppm pyrogallol, 0.51±10% ppm amino-benzoic-4 acid, 1.12±10% ppm OH-tyrosol-3, 2.98±10% ppm protocatahuic acid, 9.05±10% ppm catechein, 3.16±10% ppm chlorogenic acid, 10.22±10% ppm catechol, 6.33±10% ppm epicatechein, 2.87±10% ppm caffeine, 4.67±10% ppm p-OH-benzoic acid, 4.56±10% ppm caffeic acid, 8.21±10% ppm vanillic acid, 6.51±10% ppm p-coumaric acid, 3.02±10% ppm ferulic acid, 4.58±10% ppm iso-ferulic acid, 2.68±10% ppm resveratrol, 147.65±10% ppm e-vanillic acid, 49.91±10% ppm ellagic acid, 16.82±10% ppm alpha-coumaric acid, 102.94±10% ppm benzoic acid, 14.26±10% ppm methoxy-cinnamic-3,4,5 acid, 6.04±10% ppm coumarin, 21.42±10% ppm salicylic acid, 4.04 ppm±10% cinnamic acid, and 41.47±10% ppm thymol;

wherein the anti-microbial composition is obtained by extracting a *Boswellia serrata* gum-resin with an aqueous-ethanol solution containing 35-65 wt % water and 65-35 wt % ethanol to form a *Boswellia serrata* aqueous-ethanol extract, removing the water and the ethanol from the *Boswellia serrata* aqueous-ethanol extract to produce the *Boswellia serrata* extract, and mixing the *Boswellia serrata* extract with a solvent to form the anti-microbial composition.

2. The method of claim 1, wherein the antimicrobial composition comprises 0.1 to 10 wt % of the *Boswellia serrata* extract.

3. The method of claim 1, wherein said anti-microbial composition comprises 1.09 ppm gallic acid, 33.09 ppm pyrogallol, 0.51 ppm amino-benzoic-4 acid, 1.12 ppm OH-tyrosol-3, 2.98 ppm protocatahuic acid, 9.05 ppm catechein, 3.16 ppm chlorogenic acid, 10.22 ppm catechol, 6.33 ppm epicatechein, 2.87 ppm caffeine, 4.67 ppm p-OH-benzoic acid, 4.56 ppm caffeic acid, 8.21 ppm vanillic acid, 6.51 ppm p-coumaric acid, 3.02 ppm ferulic acid, 4.58 ppm iso-ferulic acid, 2.68 ppm resveratrol, 147.65 ppm e-vanillic acid, 49.91 ppm ellagic acid, 16.82 ppm alpha-coumaric acid, 102.94 ppm benzoic acid, 14.26 ppm methoxy-cinnamic-3,4,5 acid, 6.04 ppm coumarin, 21.42 ppm salicylic acid, 4.04 ppm cinnamic acid, and 41.47 ppm thymol.

4. The method of claim 1, wherein said anti-microbial composition comprises 4.188 ppm luteolin, 7.55 ppm narengin, 3.3873 ppm rutin, 10.847 ppm hisperidin, 5.3906 ppm rosmarinic, 1.2138 ppm quercetrin, 5.7968 quercetin, 12.058 ppm hispertin, 1.8054 ppm kampferol, 1.5162 ppm apegnin, and 1.8481 ppm 7-OH-hydroxyflavone.

* * * * *